United States Patent [19]
Holly et al.

[11] Patent Number: 5,989,537
[45] Date of Patent: Nov. 23, 1999

[54] METHODS FOR STIMULATING GRANULOCYTE/MACROPHAGE LINEAGE USING THROMBOPOIETIN

[75] Inventors: Richard D. Holly; Si Lok; Donald C. Foster; Frederick S. Hagen, all of Seattle; Kenneth Kaushansky, Woodinville; Joseph L. Kuijper, Bothell; Catherine E. Lofton-Day, Brier; Pieter J. Oort, Seattle, all of Wash.

[73] Assignees: ZymoGenetics, Inc.; University of Washington, both of Seattle, Wash.

[21] Appl. No.: 08/484,257

[22] Filed: Jun. 7, 1995

Related U.S. Application Data

[63] Continuation-in-part of application No. 08/252,491, Jun. 1, 1994, which is a continuation-in-part of application No. 08/215,203, Mar. 21, 1994, abandoned, which is a continuation-in-part of application No. 08/203,197, Feb. 25, 1994, abandoned, which is a continuation-in-part of application No. 08/196,025, Feb. 14, 1994, abandoned.

[51] Int. Cl.$^6$ ..................................................... A61K 38/19
[52] U.S. Cl. ................... 424/85.1; 424/198.1; 435/69.5; 530/351
[58] Field of Search ..................................... 530/351, 399; 424/85.1, 85.2, 198.1; 435/69.1, 69.5

[56] References Cited

U.S. PATENT DOCUMENTS

| | | | |
|---|---|---|---|
| 5,154,921 | 10/1992 | Sager et al. | 530/351 |
| 5,571,686 | 11/1996 | Rosenberg et al. | 435/29 |

FOREIGN PATENT DOCUMENTS

95/28907  11/1995  WIPO.

OTHER PUBLICATIONS

Shimosaka et al., 9th Symposium Molecular Biology of Hematopoiesis Abstract No. 9/11:211, 1995.
Eaton et al., *Blood* 84(10) Suppl. 1, Abstract No. 948, 241a, 1994.
de Sauvage et al., *Blood* 84(10) Suppl. 1, Abstract No. 1546, 390a, 1994.
Miyazaki et al., *Blood* 84(10) Suppl. 1, Abstract No. 955, 242a, 1994.
Broudy et al., *Blood* 84(10) Suppl. 1, Abstract No. 1304, 330a, 1994.
Solberg et al., *Blood* 84(10) Suppl. 1, Abstract No. 1305, 330a, 1994.
Bartley et al., *Cell* 77: 1117–1124, 1994.
Dutton, *Genetic Engineering News*: 8, 1994.
Souyri et al., *Cell* 63: 1137–1147, 1990.
Methia et al., *Blood* 82: 1395–1401, 1993.
Vigon et al., *Oncogene* 8: 2607–2615, 1993.
McDonald, *Am. J. Ped. Hematol./Oncol.* 14: 8–21, 1992.
Dessypris et al., *Chem. Abstr.* 113(10) Abstract No. 170137u: 543, Nov. 5, 1990.
A. Grossmann et al., Blood 88(9):3363–3370, Nov. 1, 1996.

*Primary Examiner*—Lorraine Spector
*Attorney, Agent, or Firm*—Deborah A. Sawislak

[57] ABSTRACT

Methods for stimulating granulocyte/macrophage lineage cells using thrombopoietin are provided. The methods provided may be used to stimulate granulocyte/macrophage progenitors and neutrophils in bone marrow and peripheral blood cells and in vitro and in vivo. In addition, methods for treatment of neutropenia in patients are disclosed.

5 Claims, 2 Drawing Sheets

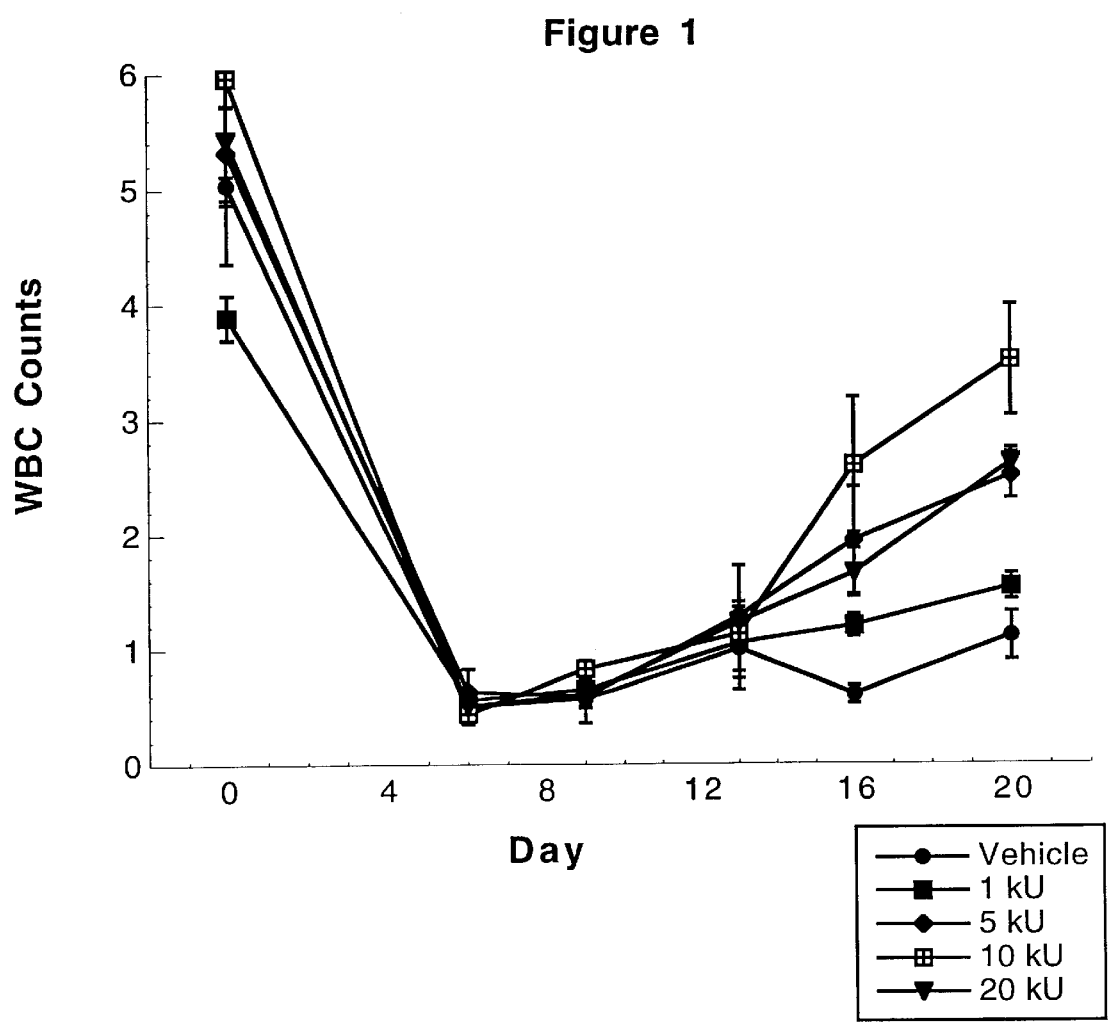

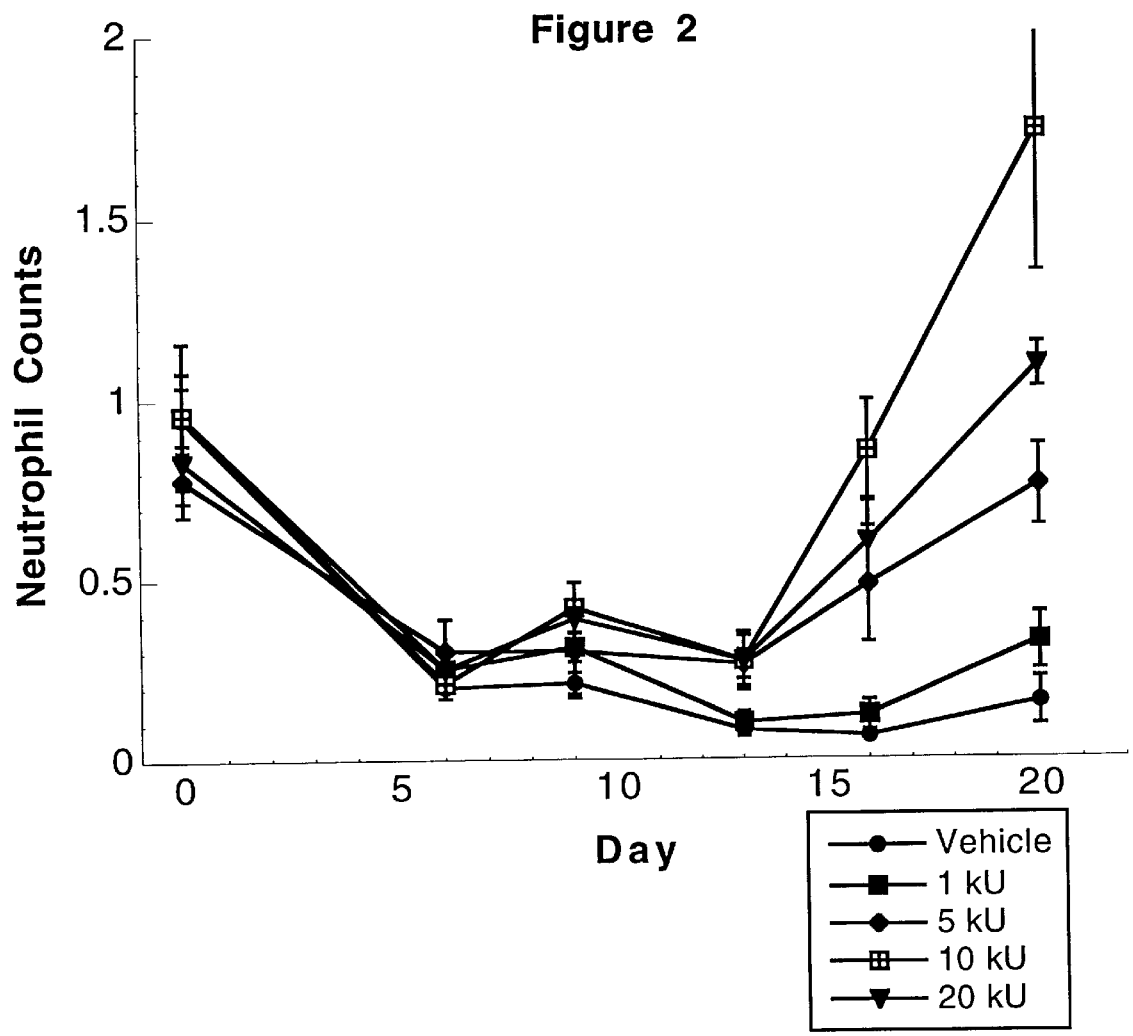

METHODS FOR STIMULATING GRANULOCYTE/MACROPHAGE LINEAGE USING THROMBOPOIETIN

CROSS REFERENCE TO RELATED APPLICATION

This application is a continuation-in-part of Ser. No. 08/252,491, filed on Jun. 1, 1994, which pending, which is a continuation-in-part of Ser. No. 08/215,203, filed Mar. 21, 1994, which is abandoned, which is a continuation-in-part of Ser. No. 08/203,197, filed Feb. 25, 1994, which is abandoned, which is a continuation-in-part of Ser. No. 0. 08/196,025, filed Feb. 14, 1994, which is abandoned, which applications are incorporated herein by reference.

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on the target cells. Cytokine action results in cellular proliferation and differentiation, with response to a particular cytokine often being lineage-specific and/or stage-specific. Development of a single cell type, such as a platelet or a neutrophil, from a stem cell may require the coordinated action of a plurality of cytokines acting in the proper sequence.

The known cytokines include the interleukins, such as IL-1, IL-2, IL-3, IL-6, IL-8, etc.; and the colony stimulating factors, such as G-CSF, M-CSF, GM-CSF, erythropoietin (EPO), etc. In general, the interleukins act as mediators of immune and inflammatory responses. The colony stimulating factors stimulate the proliferation of marrow-derived cells, activate mature leukocytes, and otherwise form an integral part of the host's response to inflammatory, infectious, and immunologic challenges.

Various cytokines have been developed as therapeutic agents. For example, erythropoietin, which stimulates the development of erythrocytes, is used in the treatment of anemia arising from renal failure. Several of the colony stimulating factors have been used in conjunction with cancer chemotherapy to speed the recovery of patients' immune systems. Interleukin-2, α-interferon and γ-interferon are used in the treatment of certain cancers. Factors responsible for stimulation of megakaryocytopoiesis and thrombocytopoiesis resisted definitive characterization, due in part to lack of a reliable source, a lack of convenient assays, and a lack of knowledge as to the site(s) of production until recently, despite three decades of work to isolate and characterize them. The megakaryocytopoietic factor referred to in the literature as "thrombopoietin" (recently reviewed by McDonald, *Exp. Hematol.* 16:201–205, 1988; and McDonald, *Am. J. Ped. Hematol. Oncol.* 14:8–21, 1992) has now been identified and isolated (see copending U.S. patent application Ser. No. 08/252,491; Lok et al., *Nature* 369:565–568, 1994; and Kaushansky et al., *Nature* 369:568–571, 1994; all herein incorporated by reference).

Mild bleeding disorders (MBDs) associated with platelet dysfunctions are relatively common (Bachmann, *Seminars in Hematology* 17: 292–305, 1980), as are a number of congenital disorders of platelet function, including Bernard-Soulier syndrome (deficiency in platelet GPIb), Glanzmann's thrombasthenia (deficiency of GPIIb and GPIIIa), congenital afibrinogenemia (diminished or absent levels of fibrinogen in plasma and platelets), and gray platelet syndrome (absence of α-granules). In addition there are a number of disorders associated with platelet secretion, storage pool deficiency, abnormalities in platelet arachidonic acid pathway, deficiencies of platelet cyclooxygenase and thromboxane synthetase and defects in platelet activation (reviewed by Rao and Holmsen, *Seminars in Hematology* 23: 102–118, 1986). At present, the molecular basis for most of these defects is not well understood.

Leukopenia is a deficiency in one or more of the cell-types collectively known as white blood cells (WBCs). Included are cells from the myeloid and lymphoid lineage. Lymphoid cells are T-cells and B-cells and their progenitors. Myeloid lineage cells include: the granulocyte/macrophage (GM) progenitor cells, which through the process known as differentiation, mature into neutrophils, monocytes, macrophages, eosinophils and basophils. The myeloid lineage white blood cells generally function as phagocytes and remove foreign material (e.g. fungi, bacteria and virus) by digestion using enzymes that are either released extracellularly or by endocytosis and degradation inside the cell.

A WBC count generally measures all the WBCs and a normal value is in the range of 5.0 to $10.0 \times 10^9$/liter. Clinically significant deficiencies of WBCs are usually deficiencies in neutrophils (neutropenia) or lymphocytes (lymphocytopenia). Levels of neutrophils and lymphocytes can be identified by differential white blood cell counts which evaluate each cell type in the WBC fraction separately. Neutropenia is diagnosed in patients with neutrophil levels below $2.0 \times 10^9$/liter. For discussion of the clinical aspects of neutropenia, see, for example, *Cecil Textbook of Medicine* (Wyngaarden et al. (eds.), 19th edition, W.B. Saunders Co., Philadephia, Pa., 1992). Neutrophil levels below $0.5 \times 10^9$/liter are considered life-threatening, resulting in serious recurrent and often difficult-to-treat infections. Abnormalities in the bone marrow account for the majority of clinically significant neutropenias and are primarily caused by cytotoxic drugs, radiation, marrow invasion by abnormal cells and infections.

While many cytokines have been characterized and some have proven clinical applications, there remains a need in the art for additional agents that stimulate proliferation and differentiation of myeloid and lymphoid precursors and the production of mature blood cells. There is a particular need for agents that stimulate the development and proliferation of cells of the multiple myeloid lineage. There is a further need in the art for agents that can be used in the treatment of cytopenias, including thrombocytopenia (low number of circulating platelets, less than about $1 \times 10^5$ platelets/mm$^3$), anemias and leukopenias, particularly neutropenia, and other platelet disorders. The present invention fulfills these needs and provides other, related advantages.

SUMMARY OF THE INVENTION

The present invention provides methods of stimulating proliferation of neutrophils comprising administering to a mammal having neutropenia, an amount of thrombopoietin (TPO) sufficient to produce a clinically significant increase in the number of neutrophils in said mammal. In another embodiment, the amount of TPO administered is in the amount of 0.1–100 μg/kg/day. In another embodiment, the number of neutrophils is increased to at least $2.0 \times 10^9$/liter.

In another aspect, the present invention provides for methods of stimulating proliferation of neutrophils comprising administering to a mammal having neutropenia, an amount of TPO in combination with a cytokine selected from the group consisting of EPO, GM-CSF, IL-3, G-CSF, SCF, IL-6 and IL-11, sufficient to produce a clinically significant increase in the number of neutrophils in said mammal, as compared to proliferation of neutrophils when administering the cytokines in the absence of TPO. In another embodiment, the number of neutrophils is increased to at least $2.0 \times 10^9$/liter. In another embodiment, the amount of TPO is 0.1–100 μg/kg/day.

In another aspect, the present invention provides methods for the ex vivo stimulation of granulocyte/macrophage progenitor cells or neutrophils comprising culturing bone marrow or peripheral blood cells with a composition comprising an amount of TPO sufficient to produce an increase in the number of granulocyte/macrophage progenitor cells or neutrophils in the bone marrow or peripheral blood cells as compared to bone marrow or peripheral blood cells cultured in the absence of TPO. In another embodiment the amount of TPO is 10 pg/ml to 10 ng/ml.

In another aspect, the present invention provides methods for the ex vivo stimulation of granulocyte/macrophage progenitor cells or neutrophils comprising culturing bone marrow or peripheral blood cells with a composition comprising an amount of TPO and G-CSF sufficient to produce an increase in the number of granulocyte/macrophage progenitor cells or neutrophils in the bone marrow or peripheral blood cells as compared to bone marrow or peripheral blood cells cultured in the absence of TPO. In another embodiment the amount of TPO is 10 pg/ml to 10 ng/ml and the amount of G-CSF is 10–1000 ng/ml.

In another aspect, the present invention provides methods for the ex vivo stimulation of granulocyte/macrophage progenitor cells or neutrophils comprising culturing bone marrow or peripheral blood cells with a composition comprising an amount of TPO in combination with a cytokine selected from the group consisting of EPO, GM-CSF, IL-3, G-CSF, SCF, IL-6 and IL-11, sufficient to produce an increase in the number of granulocyte/macrophage progenitor cells or neutrophils in the bone marrow or peripheral blood cells as compared to bone marrow or peripheral blood cells cultured in the absence of TPO. In another embodiment the amount of TPO is 10 pg/ml.

BRIEF DESCRIPTION OF THE DRAWINGS

FIG. 1 illustrates that in myelosuppressed mice WBC counts are reduced after combined radiation/carboplatin treatment and that TPO-treated animals have an earlier recovery of white blood cells relative to untreated animals.

FIG. 2 illustrates that TPO-treated animals have increased levels of neutrophils when compared to animals receiving vehicle. Neutrophil recovery started at day 13 in the animals administered 5 kU/kg/day or higher doses of TPO, whereas vehicle treated animals did not begin recovery of neutrophil counts until between day 15 and day 20.

DETAILED DESCRIPTION OF THE INVENTION

Prior to describing the present invention in detail, it may be helpful to define certain terms used herein:

Allelic variant: An alternative form of a gene that arises through mutation, or an altered polypeptide encoded by the mutated gene. Gene mutations can be silent (no change in the encoded polypeptide) or may encode polypeptides having altered amino acid sequence.

cDNA: Complementary DNA, prepared by reverse transcription of a messenger RNA template, or a clone or amplified copy of such a molecule. Complementary DNA can be single-stranded or double-stranded.

Expression vector: A DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both. The term "operably linked" indicates that the segments are arranged so that they function in concert for their intended purposes, e.g. transcription initiates in the promoter and proceeds through the coding segment to the terminator.

Gene: A segment of chromosomal DNA that encodes a polypeptide chain. A gene includes one or more regions encoding amino acids, which in some cases are interspersed with non-coding "intervening sequences" ("introns"), together with flanking, non-coding regions which provide for transcription of the coding sequence.

Molecules complementary to: Polynucleotide molecules having a complementary base sequence and reverse orientation as compared to a reference sequence. For example, the sequence 5' ATGCACGGG 3' is complementary to 5' CCCGTGCAT 3'.

Promoter: The portion of a gene at which RNA polymerase binds and mRNA synthesis is initiated.

As noted above, the present invention provides materials and methods for use in producing proteins having hematopoietic activity. As used herein, the term "hematopoietic" denotes the ability to stimulate the proliferation and/or differentiation of myeloid or lymphoid precursors as determined by standard assays. See, for example, Metcalf, *Proc. Natl. Acad. Sci. USA* 77: 5327–5330, 1980; Metcalf et al.,*J. Cell. Physiol.* 116: 198–206, 1983; and Metcalf et al., *Exp. Hematol.* 15: 288–295, 1987. Typically, marrow cells are incubated in the presence of a test sample and a control sample. The cultures are then scored for cell proliferation and differentiation by visual examination and/or staining. A particularly preferred assay is the MTT colorimetric assay of Mosman (*J. Immunol. Meth.* 65: 55–63, 1983; incorporated herein by reference) disclosed in more detail in the examples which follow.

The present invention is based in part upon the discovery that thrombopoietin (TPO) stimulates myeloid cell growth, particularly of granulocyte/macrophage lineage cells. Granulocyte/macrophage progenitors are cells of the myeloid lineage that mature as neutrophils, monocytes, basophils and eosinophils. When the present inventors administered TPO to myelosuppressed mammals, in addition to an increase in platelets, surprisingly TPO was found to augment the recovery of granulocyte/macrophage progenitors, neutrophils, monocytes and basophils resulting in a reduction of the duration of degree of leukopenia.

The identification of thrombopoietin is based in part upon the discovery of an activity that stimulates cell growth via the MPL receptor. This receptor (Souyri et al., *Cell* 63: 1137–1147, 1990) was, prior to this discovery, an "orphan" receptor whose natural ligand was unknown. Through processes of cloning and mutagenesis, the inventors developed a cell line that was dependent upon stimulation of an MPL receptor-linked pathway for its survival and growth, and which was capable of autocrine stimulation of the receptor. Conditioned media from these interleukin-3 (IL-3) independent cells was found to support the growth of cells that expressed the MPL receptor and were otherwise dependent on IL-3. Antibody neutralization experiments demonstrated that this activity was not due to IL-3 or IL-4, and that it could be neutralized by a soluble form of the MPL receptor. A cDNA library was then prepared from the IL-3 independent cell line. The DNA was used to transfect baby hamster kidney (BHK) cells, and media from the transfectants were assayed for the ability to stimulate MPL-dependent cell proliferation. A positive clone was isolated, and recombinant MPL ligand was produced. The recombinant protein was found to stimulate the proliferation of a broad spectrum of myeloid and lymphoid precursors, and, in particular, to stimulate production of megakaryocytes and neutrophils from progenitor cells in the bone marrow. In addition, the recombinant protein was found to stimulate the production of platelets in test animals. In view of these activities, the protein has been designated thrombopoietin (TPO).

The methods of the present invention utilize isolated polynucleotide molecules encoding thrombopoietin. Useful polynucleotide molecules in this regard include mRNA, genomic DNA, cDNA, synthetic DNA and DNA molecules generated by ligation of fragments from different sources. For production of recombinant TPO, DNA molecules lacking introns are preferred for use in most expression systems. By "isolated" it is meant that the molecules are removed from their natural genetic milieu. Thus, the DNA molecules are free of other genes with which they are ordinarily associated. In particular, the molecules are free of extraneous or unwanted coding sequences, and in a form suitable for use within genetically engineered protein production systems.

The sequences of cDNA clones encoding representative mouse and human TPO proteins are shown in SEQ ID NO: 1 and SEQ ID NO: 18, respectively, and the corresponding amino acid sequences are shown in SEQ ID NO: 2 and SEQ ID NO: 19, respectively. Those skilled in the art will recognize that the sequences shown in SEQ ID NOS: 1, 2, 18 and 19, and the genomic sequences shown in SEQ ID NOS: 20 and 21, correspond to single alleles of the murine or human gene, and that allelic variation is expected to exist. Allelic variants of the DNA sequences shown in SEQ ID NO: 1, SEQ ID NO: 18 and SEQ ID NO: 20, including those containing silent mutations and those in which mutations result in amino acid sequence changes, can be used within the methods of the present invention, as are proteins which are allelic variants of SEQ ID NO: 2 and SEQ ID NO: 18. It will also be evident that one skilled in the art could engineer sites that would facilitate manipulation of the nucleotide sequence using alternative codons.

The murine and human sequences disclosed herein are useful tools for preparing isolated polynucleotide molecules encoding TPO proteins from other species ("species homologs"). Preferred such species homologs include mammalian homologs such as bovine, canine, porcine, ovine, equine and, in particular, primate proteins. Methods for using sequence information from a first species to clone a corresponding polynucleotide sequence from a second species are well known in the art. See, for example, Ausubel et al., eds., *Current Protocols in Molecular Biology*, John Wiley and Sons, Inc., New York, 1987. The DNA molecules encoding TPO are generally at least 60%, preferably at least 80%, and may be 90–95% or more identical in sequence to SEQ ID NO: 1 and SEQ ID NO: 18 and their allelic variants. Thrombopoietin molecules are characterized by their ability to specifically bind to MPL receptor from the same species and to stimulate platelet production in vivo. In normal test animals, TPO is able to increase platelet levels by 100% or more within 10 days after beginning daily administration.

Analysis of mRNA distribution showed that mRNA encoding TPO was present in several tissues of human and mouse, and was more abundant in lung, liver, heart, skeletal muscle and kidney. Thus, to isolate homologs from other species, a cDNA library is prepared, preferably from one of the tissues found to produce higher levels of the mRNA. Methods for preparing cDNA libraries are well known in the art. See, for example, Sambrook et al., eds., *Molecular Cloning: A Laboratory Manual*, 2nd ed., Cold Spring Harbor Laboratory Press, 1989 and references cited therein. To detect molecules encoding TPO, the library is then probed with the mouse or human cDNA disclosed herein or with a fragment thereof or with one or more small probes based on the disclosed sequences. Of particular utility are probes comprising an oligonucleotide of at least about 14 or more nucleotides and up to 25 or more nucleotides in length that are at least 80% identical to a same-length portion of SEQ ID NO: 1, SEQ ID NO: 18, SEQ ID NO: 20 or their complementary sequences. It is preferred to probe the library at a low hybridization stringency, i.e. about 2× SSC and a hybridization temperature of about 50° C. using labeled probes. Molecules to which the probe hybridizes are detected using standard detection procedures. Positive clones are confirmed by sequence analysis and activity assays, such as ability to bind homologous MPL receptor (i.e. an MPL receptor from the same species as the cDNA) or to stimulate hematopoiesis from homologous marrow cells. As will be evident to one skilled in the art, other cloning methods can be utilized.

Polynucleotide molecules encoding TPO (including allelic variants and species homologs of the molecules disclosed herein) can also be isolated by cloning from a cell line that produces the MPL ligand and exhibits autocrine growth stimulation. Briefly, a factor-dependent cell line is transfected to express an MPL receptor (Vigon et al., *Proc. Natl. Acad. Sci. USA* 89: 5640–5644, 1992; Skoda et al., *EMBO J*. 12: 2645–2653, 1993; and SEQ ID NO: 17), then mutagenized, and factor-independent cells are selected. These cells are then used as a source of TPO mRNA. Suitable factor-dependent cell lines include the IL-3-dependent BaF3 cell line (Palacios and Steinmetz, Cell 41: 727–734, 1985; Mathey-Prevot et al., *Mol. Cell. Biol.* 6: 4133–4135, 1986), FDC-P1 (Hapel et al., *Blood* 64: 786–790, 1984), and MO7e (Kiss et al., Leukemia 7: 235–240, 1993). Growth factor-dependent cell lines can be established according to published methods (e.g. Greenberger et al., *Leukemia Res.* 8: 363–375, 1984; Dexter et al., in Baum et al. Eds., *Experimental Hematology Today*, 8th Ann. Mtg. Int. Soc. Exp. Hematol. 1979, 145–156, 1980). In a typical procedure, cells are removed from the tissue of interest (e.g. bone marrow, spleen, fetal liver) and cultured in a conventional, serum-supplemented medium, such as RPMI 1640 supplemented with 10% fetal bovine serum (FBS), 15% horse serum and $10^{-6}$ M hydrocortisone. At one- to two-week intervals non-adherent cells are harvested, and the cultures are fed fresh medium. The harvested, non-adherent cells are washed and cultured in medium with an added source of growth factor (e.g. RPMI 1640+10% FBS+5–20% WEHI-3 conditioned medium as a source of IL-3). These cells are fed fresh medium at one- to two-week intervals and expanded as the culture grows. After several weeks to several months, individual clones are isolated by plating the cells onto semi-solid medium (e.g. medium containing methylcellulose) or by limiting dilution. Factor dependence of the clones is confirmed by culturing individual clones in the absence of the growth factor. Retroviral infection or chemical mutagenesis can be used to obtain a higher frequency of growth factor-dependent cells. The factor-dependent cells are transfected to express the MPL receptor, then mutagenized, such as by chemical treatment, exposure to ultraviolet light, exposure to x-rays, or retroviral insertional mutagenesis. The mutagenized cells are then cultured under conditions in which cell survival is dependent upon autocrine growth factor production, that is in the absence of the exogenous growth factor(s) required by the parent cell. Production of TPO is confirmed by screening, such as by testing conditioned media on cells expressing and not expressing MPL receptor or by testing the activity of conditioned media in the presence of soluble MPL receptor or antibodies against known cytokines.

$$\frac{\text{Total number of identical matches}}{[\text{length of the longer sequence plus the number of gaps introduced into the longer sequence in order to align the two sequences}]} \times 100$$

TABLE 1

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| A | 4  |    |    |    |    |    |    |    |    |    |    |    |    |    |    |    |    |    |    |   |
| R | -1 | 5  |    |    |    |    |    |    |    |    |    |    |    |    |    |    |    |    |    |   |
| N | -2 | 0  | 6  |    |    |    |    |    |    |    |    |    |    |    |    |    |    |    |    |   |
| D | -2 | -2 | 1  | 6  |    |    |    |    |    |    |    |    |    |    |    |    |    |    |    |   |
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

The methods of the present invention also utilize isolated proteins that are substantially homologous to the proteins of SEQ ID NO: 2 or SEQ ID NO: 19 and their species homologs. By "isolated" is meant a protein which is found in a condition other than its native environment, such as apart from blood and animal tissue. In a preferred form, the isolated protein is substantially free of other proteins, particularly other proteins of animal origin. It is preferred to provide the proteins in a highly purified form, i.e. greater than 95% pure, more preferably greater than 99% pure. The term "substantially homologous" is used herein to denote proteins having 50%, preferably 60%, more preferably at least 80%, sequence identity to the sequences shown in SEQ ID NO: 2 or SEQ ID NO: 19 or their species homologs. Such proteins will more preferably be at least 90% identical, and most preferably 95% or more identical to SEQ ID NO: 2 or SEQ ID NO: 19 or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes). The percent identity is then calculated as:

Substantially homologous proteins are characterized as having one or more amino acid substitutions, deletions or additions. These changes are preferably of a minor nature, that is conservative amino acid substitutions that do not significantly affect the folding or activity of the protein (see Table 2); small deletions, typically of one to about 30 amino acids; and small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See, in general Ford et al., *Protein Expression and Purification* 2: 95–107, 1991, which is incorporated herein by reference.

TABLE 2

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

Essential amino acids in TPO may be identified according to procedures known in the art, such as site-directed mutagenesis or alanine-scanning mutagenesis (Cunningham and Wells, Science 244, 1081–1085, 1989). In the latter technique, single alanine mutations are introduced at every residue in the molecule, and the resultant mutant molecules are tested for biological activity (e.g. receptor binding, in vitro or in vivo proliferative activity) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

In general, cytokines are predicted to have a four-alpha helix structure, with the first and fourth helices being most important in ligand-receptor interactions and more highly conserved among members of the family. Referring to the human TPO amino acid sequence shown in SEQ ID NO: 19, alignment of cytokine sequences suggests that these helices are bounded by amino acid residues 29 and 53, 80 and 99, 108 and 130, and 144 and 168, respectively (boundaries are ±4 residues). Helix boundaries of the mouse (SEQ ID NO: 2) and other non-human TPOs can be determined by alignment with the human sequence. Other important structural aspects of TPO include the cysteine residues at positions 51, 73, 129 and 195 of SEQ ID NO: 2 (corresponding to positions 28, 50, 106 and 172 of SEQ ID NO: 19).

In addition, the proteins (or polypeptide fragments thereof) can be joined to other bioactive molecules, particularly other cytokines, to provide multi-functional molecules. For example, the C-terminal domain of thrombopoietin can be joined to other cytokines to enhance their biological properties or efficiency of production. The thrombopoietin molecule appears to be composed of two domains. The first (amino-terminal) domain of approximately 150 amino acids is similar in size and bears structural resemblance to erythropoietin and several other hematopoietic cytokines. Following this first domain is a second domain of approximately 180 amino acids, which has a structure that is not significantly similar to any known protein structure in databases. This second domain is highly enriched in N-linked glycosylation sites and in serine, proline, and threonine residues, which are hallmarks of O-linked glycoslyation sites. This apparently high carbohydrate content suggests that this domain plays a role in making the hydrophobic first domain relatively more soluble. Experimental evidence indicates that the carbohydrate associated with the second domain is involved in proper intracellular assembly and secretion of the protein during its biosynthesis. The second domain may also play a role in stabilizing the first domain against proteolytic degradation and/or prolonging the in vivo half-life of the molecule, and may potentiate biological signal transmittance or specific activity of the protein.

In addition to the hematopoietic proteins disclosed above, fragments of these proteins and isolated polynucleotide molecules encoding the fragments can be used within the present invention. Of particular interest are fragments of at least 10 amino acids in length that bind to an MPL receptor, and polynucleotide molecules of at least 30 nucleotides in length encoding such polypeptides. Polypeptides of this type are identified by known screening methods, such as by digesting the intact protein or synthesizing small, overlapping polypeptides or polynucleotides (and expressing the latter), optionally in combination with the techniques of structural analysis disclosed above. The resultant polypeptides are then tested for the ability to specifically bind the MPL receptor and stimulate cell proliferation via the MPL receptor. Binding is determined by conventional methods, such as that disclosed by Klotz, Science 217: 1247, 1982 ("Scatchard analysis"). Briefly, a radiolabeled test polypeptide is incubated with MPL receptor-bearing cells in the presence of increasing concentrations of unlabeled TPO. Cell-bound, labeled polypeptide is separated from free labeled polypeptide by centrifugation through phthalate oil. The binding affinity of the test polypeptide is determined by plotting the ratio of bound to free label on the ordinate versus bound label on the abscissa. Binding specificity is determined by competition with cytokines other than TPO. Receptor binding can also be determined by precipitation of the test compound by immobilized MPL receptor (or the ligand-binding extracellular domain thereof). Briefly, the receptor or portion thereof is immobilized on an insoluble support. The test compound is labeled, e.g. by metabolically labeling of the host cells in the case of a recombinant test compound, or by conventional, in vitro labeling methods (e.g. radio-iodination). The labeled compound is then combined with the immobilized receptor, unbound material is removed, and bound, labeled compound is detected. Methods for detecting a variety of labels are known in the art. Stimulation of proliferation is conveniently determined using the MTT colorimetric assay with MPL receptor-bearing cells. Polypeptides are assayed for activity at various concentrations, typically over a range of 1 nm to 1 mM.

Larger polypeptides of up to 50 or more residues, preferably 100 or more residues, more preferably about 140 or more residues, up to the size of the entire mature protein can also be used. For example, analysis and modeling of the amino acid sequence shown in SEQ ID NO: 2 from residue 51 to residue 195, inclusive, or SEQ ID NO: 19 from residue 28 to residue 172, inclusive, suggest that these portions of the molecules are cytokine-like domains capable of self assembly. Also of interest are molecules containing this core cytokine-like domain plus one or more additional segments or domains of the primary translation product. Thus, other polypeptides of interest include those shown in Table 3.

TABLE 3

Mouse TPO (SEQ ID NO:2):

Cys (residue 51)--Val (residue 196)
Cys (51)--Pro (206)
Cys (51)--Thr (379)
Ser (45)--Cys (195)
Ser (45)--Val (196)
Ser (45)--Pro (206)
Ser (45)--Thr (379)
Met (24)--Cys (195)
Met (24)--Val (196)
Met (24)--Pro (206)
Met (24)--Thr (379)
Met (1)--Cys (195)
Met (1)--Val (196)
Met (1)--Pro (206)
Met (1)--Thr (379)

Human TPO (SEQ ID NO:19)

Cys (28)--Val (173)
Cys (28)--Arg (175)
Cys (28)--Gly (353)
Ser (22)--Cys (172)
Ser (22)--Val (173)
Ser (22)--Arg (175)
Ser (22)--Gly (353)
Met (1)--Cys (172)
Met (1)--Val (173)
Met (1)--Arg (175)
Met (1)--Gly (353)

Those skilled in the art will recognize that intermediate forms of the molecules (e.g those having C-termini between residues 196 and 206 of SEQ ID NO:2 or those having N-termini between residues 22 and 28 of SEQ ID NO: 19) are also of interest, as are polypeptides having one or more amino acid substitutions, deletions, insertions, or N- or C-terminal extensions as disclosed above. Thus, the methods of the present invention can utilize hematopoietic polypeptides of at least 10 amino acid residues, preferably at least 50 residues, more preferably at least 100 residues and most preferably at least about 140 residues in length, wherein said polypeptides are substantially homologous to like-size polypeptides of SEQ ID NO: 2 or SEQ ID NO: 19.

TPO proteins can be produced in genetically engineered host cells according to conventional techniques. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

In general, a DNA sequence encoding a TPO molecule is operably linked to a transcription promoter and terminator within an expression vector. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements commercial suppliers.

To direct a TPO protein into the secretory pathway of the host cells, a secretory signal sequence (also known as a leader sequence, prepro sequence or pre sequence) is provided in the expression vector. The secretory signal sequence is joined to the DNA sequence encoding a TPO protein in the correct reading frame. Secretory signal sequences are commonly positioned 5' to the DNA sequence encoding the protein of interest, although certain signal sequences may be positioned elsewhere in the DNA sequence of interest (see, e.g., Welch et al., U.S. Pat. No. 5,037,743; Holland et al., U.S. Pat. No. 5,143,830). The secretory signal sequence may be that normally associated with TPO, or may be from a gene encoding another secreted protein.

Yeast cells, particularly cells of the genus Saccharomyces, are a preferred host. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. A preferred secretory signal sequence for use in yeast is that of the *S. cerevisiae* MFα1 gene (Brake, ibid.; Kurjan et al., U.S. Pat. No. 4,546,082). Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–3465, 1986 and Cregg, U.S. Pat. No. 4,882,279.

Other fungal cells are also suitable as host cells. For example, Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming *Neurospora* are disclosed by Lambowitz, U.S. Pat. No. 4,486,533, which is incorporated herein by reference.

Cultured mammalian cells are also preferred hosts. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982) and DEAE-dextran mediated transfection (Ausubel et al., eds., *Current Protocols in Molecular Biology*, John Wiley and Sons, Inc., NY, 1987), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate.

Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign proteins therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (*Bangalore*) 11:47–58, 1987.

Preferred prokaryotic host cells for use in carrying out the present invention are strains of the bacteria *Escherichia coli*, although Bacillus and other genera are also useful. Techniques for transforming these hosts and expressing foreign DNA sequences cloned therein are well known in the art (see, e.g., Sambrook et al., ibid.). When expressing the proteins in bacteria such as *E. coli*, the protein may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate. The denatured protein is then refolded by diluting the denaturant. In the latter case, the protein can be recovered from the periplasmic space in a soluble and functional form by disrupting the cells (by, for example, sonication or osmotic shock) to release the contents of the periplasmic space and recovering the protein.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Transgenic animal technology may be employed to produce TPO. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (from about 1 to 15 g/l).

From a commercial point of view, it is clearly preferable to use as the host a species that has a large milk yield. While smaller animals such as mice and rats can be used (and are preferred at the proof-of-concept stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), beta-lactoglobulin, α-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene. See Whitelaw et al., *Biochem J.* 286: 31–39, 1992. Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836–840, 1988; Palmiter et al., *Proc. Natl. Acad. Sci. USA* 88: 478–482, 1991; Whitelaw et al., *Transgenic Res.* 1: 3–13, 1991; WO 89/01343; WO 91/02318). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. one such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. The region surrounding the initiation ATG of the TPO sequence can be replaced with corresponding sequences from a milk specific protein gene. Such replacement provides a putative tissue-specific initiation environment to enhance expression. It is convenient to replace the entire TPO pre-pro and 5' non-coding sequences with those of, for example, the BLG gene, although smaller regions may be replaced.

For expression of TPO in transgenic animals, a DNA segment encoding TPO is operably linked to additional DNA segments required for its expression to produce expression units. Such additional segments include the above-mentioned promoter, as well as sequences which provide for termination of transcription and polyadenylation of mRNA. The expression units will further include a DNA segment encoding a secretory signal sequence operably linked to the segment encoding TPO. The secretory signal sequence may be a native TPO secretory signal sequence or may be that of another protein, such as a milk protein. See, for example, von Heinje, *Nuc. Acids Res.* 14: 4683–4690, 1986; and Meade et al., U.S. Pat. No. 4,873,316, which are incorporated herein by reference.

Construction of expression units for use in transgenic animals is conveniently carried out by inserting a TPO sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a TPO polypeptide, thereby creating a gene fusion that includes the expression control sequences of the milk protein gene. In any event, cloning of the expression units in plasmids or other vectors facilitates the amplification of the TPO sequence. Amplification is conveniently carried out in bacterial (e.g. *E. coli*) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468–1474, 1988) or site-directed integration using embryonic stem (ES) cells (reviewed by Bradley et al., *Bio/Technology* 10: 534–539, 1992). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds.

General procedures for producing transgenic animals are known in the art. See, for example, Hogan et al., *Manipulating the Mouse Embryo: A Laboratory Manual*, Cold Spring Harbor Laboratory, 1986; Simons et al., *Bio/Technology* 6: 179–183, 1988; Wall et al., *Biol. Reprod.* 32: 645–651, 1985; Buhler et al., *Bio/Technology* 8: 140–143, 1990; Ebert et al., *Bio/Technology* 9: 835–838, 1991; Krimpenfort et al., *Bio/Technology* 9: 844–847, 1991; Wall et al., *J. Cell. Biochem.* 49: 113–120, 1992; U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., *Proc. Natl. Acad. Sci. USA* 77: 7380–7384, 1980; Gordon and Ruddle, *Science* 214: 1244–1246, 1981; Palmiter and Brinster, *Cell* 41: 343–345, 1985;

Brinster et al., *Proc. Natl. Acad. Sci. USA* 82: 4438–4442, 1985; and Hogan et al. (ibid.). These techniques were subsequently adapted for use with larger animals, including livestock species (see e.g., WIPO publications WO 88/00239, WO 90/05188, and WO 92/11757; and Simons et al., *Bio/Technology* 6: 179–183, 1988). To summarize, in the most efficient route used to date in the generation of transgenic mice or livestock, several hundred linear molecules of the DNA of interest are injected into one of the pro-nuclei of a fertilized egg according to techniques which have become standard in the art. Injection of DNA into the cytoplasm of a zygote can also be employed.

Production in transgenic plants may also be employed. Expression may be generalized or directed to a particular organ, such as a tuber. See, Hiatt, *Nature* 344:469–479, 1990; Edelbaum et al., *J. Interferon Res.* 12:449–453, 1992; Sijmons et al., *Bio/Technolocy* 8:217–221, 1990; and European Patent Office Publication EP 255,378.

TPO is purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography on concanavalin A or other lectin, thereby making use of the carbohydrate present on the protein. The proteins can also be purified using an immobilized MPL receptor protein or ligand-binding portion thereof or through the use of an affinity tag (e.g. polyhistidine, substance P or other polypeptide or protein for which an antibody or other specific binding agent is available). A specific cleavage site may be provided between the protein of interest and the affinity tag.

TPO can be used therapeutically wherever it is desirable to increase proliferation of cells in the bone marrow, such as in the treatment of cytopenia, such as that induced by aplastic anemia, myelodisplastic syndromes, chemotherapy or congenital cytopenias. The proteins are also useful for increasing platelet production, such as in the treatment of thrombocytopenia.

Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. TPO can reduce or eliminate the need for transfusions, thereby reducing the incidence of platelet alloimmunity. Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for TPO include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

In addition to stimulating the proliferation of megakaryocytes and increasing platelets, TPO has been found to increase granulocyte/macrophage progenitors, resulting in the increased numbers of cells maturing from this lineage. Of particular interest, is the increase in neutrophils.

For pharmaceutical use, hematopoietic proteins are formulated for parenteral, particularly intravenous or subcutaneous, delivery according to conventional methods. Intravenous administration will be by bolus injection or infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, the TPO proteins may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in Remington's Pharmaceutical Sciences, Gennaro, ed., Mack Publishing Co., Easton Pa., 1990, which is incorporated herein by reference. Therapeutic doses will generally be in the range of 0.1 to 100 μg/kg of patient weight per day, preferably 0.5–20 μg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. Such treatment has been found to cause a subsequent increase in neutrophils. Neutrophil levels that reach at least 2.0×10$^9$/liter peripheral neutrophil counts are considered clinically significant. As stated previously, neutrophil counts of less than 0.5×10$^9$/liter are considered life-threatening. More commonly, the proteins will be administered over one week or less, often over a period of one to three days.

In general, a therapeutically effective amount of TPO is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet and concurrent neutrophil disorders will thus be continued until a platelet count of at least 20,000/mm$^3$, preferably 50,000/mm$^3$ is reached. The hematopoetic proteins can also be administered in combination with other cytokines such as IL-3, –6 and –11; stem cell factor; erythropoietin; G-CSF and GM-CSF. Within regimens of combination therapy, daily doses of other cytokines will in general be: EPO, ≦150 U/kg; GM-CSF, 5–15 μg/kg; IL-3, 1–5 μg/kg; and G-CSF, 1–25 μg/kg. Combination therapy with G-CSF, GM-CSF, IL-3 or a combination thereof, for example, is indicated in patients with low neutrophil levels.

TPO proteins are also valuable tools for the in vitro study of the differentiation and development of hematopoietic cells, such as for elucidating the mechanisms of cell differentiation and for determining the lineages of mature cells, and may also find utility as proliferative agents in cell culture.

TPO can also be used ex vivo, such as in autologous marrow culture. Briefly, bone marrow is removed from a patient prior to chemotherapy and treated with TPO, optionally in combination with one or more other cytokines. The treated marrow is then returned to the patient after chemotherapy to speed the recovery of the marrow. In addition, TPO can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with TPO, optionally in combination with one or more other cytokines, including but not limited to SCF, G-CSF, IL-3, GM-CSF, IL-6 or IL-11, to differentiate and proliferate into high-density megakaryocyte and granulocyte/macrophage progenitor cultures, which can then be returned to the patient following high-dose chemotherapy.

The invention is further illustrated by the following non-limiting examples.

EXAMPLE I

Isolation of Human MPL Receptor cDNAs

Human MPL-P and MPL-K receptor isoform encoding cDNAs were isolated from human erythroid leukemic (HEL) cells (Martin and Papayannopoulu, Science 216: 1233–1235, 1982) by reverse transcriptase polymerase chain reaction (PCR) employing primers made to the published sequence encoding the amino and carboxyl termini of the receptors (Vigon et al., Proc. Natl. Acad. Sci. USA 89: 5640–5644, 1992). Template HEL cell cDNA was synthesized from poly d(T)-selected poly(A)$^+$ RNA using primer ZC5499 (SEQ ID NO: 3). Thirteen μl of HEL cell poly(A)$^+$ RNA at a concentration of 1 μg/pl was mixed with 3 μl of 20 pmole/μl first strand primer ZC5499 (SEQ ID NO: 3). The mixture was heated at 65° C. for 4 minutes and cooled by chilling on ice.

First strand cDNA synthesis was initiated by the addition of 8 μl of first strand buffer (250 mM Tris-HCl, pH 8.3, 375 mM KCl, 15 mM MgCl$_2$) (5× SUPERSCRIPT™ buffer; GIBCO BRL, Gaithersburg, Md.), 4 μl of 100 mM dithiothreitol and 3 μl of a deoxynucleotide triphosphate solution containing 10 mM each of DATP, dGTP, dTTP and 5-methyl-dCTP (Pharmacia LKB Biotechnology Inc., Piscataway, N.J.). The reaction mixture was incubated at 45° C. for 4 minutes followed by the addition of 10 μl of 200 U/μl of RNase H$^-$ reverse transcriptase (SUPERSCRIPT™ reverse transcriptase; GIBCO BRL) to the RNA-primer mixture. The reaction was incubated at 45° C. for 1 hour followed by an incubation at 50° C. for 15 minutes. Sixty μl of TE (10 mM Tris:HCl, pH 8.0, 1 mM EDTA) was added to the reaction followed by chromatography through a 400 pore size gel filtration column (CHROMA SPIN+TE-400™; Clontech Laboratories Inc., Palo Alto, Calif.) to remove excess primer.

First strand HEL cell cDNA was used as a template for the amplification of human MPL-P receptor cDNA using primers corresponding to the region encoding the amino and carboxyl termini of the receptor protein (Vigon et al., ibid.). The primers also each incorporated a different restriction enzyme cleavage site to aid in the directional cloning of the amplified product (ZC5746, SEQ ID NO: 4, containing an Eco RI site; ZC5762, SEQ ID NO: 5, containing an Xho I site). A 100 μl reaction was set up containing 10 ng of template cDNA, 50 pmoles of each primer; 200 μM of each deoxynucleotide triphosphate (Pharmacia LKB Biotechnology Inc.); 1 μl of 10× PCR buffer (Promega Corp., Madison, Wis.); and 10 units of Taq polymerase (Roche Molecular Systems, Inc., Branchburg, N.J.). The polymerase chain reaction was run for 35 cycles (1 minute at 95° C., 1 minute at 60° C. and 2 minutes at 72° C. with 1 extra second added to each successive cycle) followed by a 10 minute incubation at 72° C.

Human MPL-K receptor cDNA was isolated by polymerase chain reaction amplification from HEL cell cDNA in an manner identical to the MPL-P receptor cDNA described above, except primer ZC5762 (SEQ ID NO: 5) was replaced with ZC5742 (SEQ ID NO: 6). PCR primer ZC5742 is specific to the 3' terminus of human MPL-K cDNA and incorporated an Xho I restriction site to facilitate cloning.

The reaction products were extracted twice with phenol/chloroform (1:1), then once with chloroform and were ethanol precipitated. Following digestion with Eco RI and Xho I, the products were fractionated on a 0.8% low melt agarose gel (SEA PLAQUE GTG™ low melt agarose; FMC Corp., Rockland, ME). A 1.9 Kb amplified product corresponding to human MPL-P receptor cDNA and a 1.7 Kb product corresponding to human MPL-K receptor cDNA were recovered from the excised gel slices by digestion of the gel matrix with β-agarase I (New England Biolabs, Inc., Beverly, Mass.) followed by ethanol precipitation. The cDNAs were subcloned into the vector pBluescript® SK+

(Stratagene Cloning Systems, La Jolla, Calif.) for validation by sequencing.

EXAMPLE II

Isolation of Mouse MPL Receptor cDNA

Spleens from C57BL/KsJ-db/db mice were removed and immediately placed in liquid nitrogen. Total RNA was prepared from spleen tissue using guanidine isothiocyanate (Chirgwin et al., *Biochemistry* 18: 52–94, 1979) followed by a CsCl centrifugation step. Spleen poly(A)+ RNA was isolated using oligo d(T) cellulose chromatography (Aviv and Leder, *Proc. Natl. Acad. Sci. U.S.A.* 69: 1408–1412, 1972).

Seven and a half μl of poly d(T)-selected poly(A)+ mouse spleen RNA at a concentration of 1.7 μg/μl was mixed with 3 μl of 20 pmole/μl first strand primer ZC6091 (SEQ ID NO: 7) containing a Not I restriction site. The mixture was heated at 65° C. for 4 minutes and cooled by chilling on ice. First strand cDNA synthesis was initiated by the addition of 8 μl of 250 mM Tris-HCl, pH 8.3, 375 mM KCl, 15 mM MgCl$_2$ (5× SUPERSCRIPT™ buffer; GIBCO BRL), 4 μl of 100 mM dithiothreitol and 3 μl of a deoxynucleotide triphosphate solution containing 10 mM each of dATP, dGTP, dTTP and 5-methyl-dCTP (Pharmacia LKB Biotechnology Inc.) to the RNA-primer mixture. The reaction mixture was incubated at 45° C. for 4 minutes followed by the addition of 10 μl of 200 U/μl RNase H⁻ reverse transcriptase (GIBCO BRL). The efficiency of the first strand synthesis was analyzed in a parallel reaction by the addition of 10 μCi of $^{32}$P-αdCTP to a 10 μl aliquot of the reaction mixture to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (CHROMA SPIN+TE-400™; Clontech Laboratories Inc.). Unincorporated nucleotides in the unlabeled first strand reaction were removed by twice precipitating the cDNA in the presence of 8 μg of glycogen carrier, 2.5 M ammonium acetate and 2.5 volume ethanol. The unlabeled cDNA was resuspended in 50 μl water for use in second strand synthesis. The length of the labeled first strand cDNA was determined by agarose gel electrophoresis.

Second strand synthesis was performed on first strand cDNA under conditions that promoted first strand priming of second strand synthesis resulting in DNA hairpin formation. The reaction mixture was assembled at room temperature and consisted of 50 μl of the unlabeled first strand cDNA, 16.5 μl water, 20 μl of 5× polymerase I buffer (100 mM Tris: HCl, pH 7.4, 500 mM KCl, 25 mM MgCl$_2$, 50 mM (NH$_4$)$_2$SO$_4$), 1 μl of 100 mM dithiothreitol, 2 μl of a solution containing 10 mM of each deoxynucleotide triphosphate, 3 μl of 5 mM β-NAD, 15 μl of 3 U/μl *E. coli* DNA ligase (New England Biolabs Inc., Beverly, Mass.) and 5 μl of 10 U/μl *E. coli* DNA polymerase I (Amersham Corp., Arlington Heights, Ill.). The reaction was incubated at room temperature for 5 minutes followed by the addition of 1.5 μl of 2 U/μl RNase H (GIBCO BRL). A parallel reaction in which a 10 μl aliquot of the second strand synthesis mixture was labeled by the addition of 10 μCi $^{32}$P-αdCTP was used to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories, Inc.) before analysis by agarose gel electrophoresis. The unlabeled reaction was terminated by two extractions with phenol/chloroform and a chloroform extraction followed by ethanol precipitation in the presence of 2.5 M ammonium acetate.

The single-stranded DNA of the hairpin structure was cleaved using mung bean nuclease. The reaction mixture contained 100 μl of second strand cDNA, 20 μl of 10× mung bean nuclease buffer (Stratagene Cloning Systems, La Jolla, Calif.), 16 μl of 100 mM dithiothreitol, 51.5 μl of water and 12.5 μl of a 1:10 dilution of mung bean nuclease (Promega Corp.; final concentration 10.5 U/μl) in mung bean nuclease dilution buffer. The reaction was incubated at 37° C. for 15 minutes. The reaction was terminated by the addition of 20 μl of 1 M Tris: HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 190 μl of water, was mixed with 50 μl 5× T4 DNA polymerase buffer (250 mM Tris:HCl, pH 8.0, 250 mM KCl, 25 mM MgCl$_2$), 3 μl 0.1 M dithiothreitol, 3 μl of a solution containing 10 mM of each deoxynucleotide triphosphate and 4 μl of 1 U/μl T4 DNA polymerase (Boehringer Mannheim Corp., Indianapolis, Ind.). After an incubation of 1 hour at 10° C., the reaction was terminated by the addition of 10 μl of 0.5 M EDTA followed by serial phenol/chloroform and chloroform extractions as described above. The DNA was chromatographed through a 400 pore size gel filtration column (Clontech Laboratories Inc., Palo Alto, Calif.) to remove trace levels of protein and to remove short cDNAs less than ~400 bp in length. The DNA was ethanol precipitated in the presence of 12 μg glycogen carrier and 2.5 M ammonium acetate and was resuspended in 10 μl of water. Based on the incorporation of $^{32}$P-αdCTP, the yield of cDNA was estimated to be ~2 μg from a starting mRNA template of 12.5 μg.

Eco RI adapters were ligated onto the 5' ends of the cDNA to enable cloning into a lambda phage vector. A 10 μl aliquot of cDNA (~2μg) and 10 μl of 65 pmole/μl of Eco RI adapter (Pharmacia LKB Biotechnology Inc.) were mixed with 2.5 μl 10× ligase buffer (Promega Corp.), 1 μl of 10 mM ATP and 2 μl of 15 U/μl T4 DNA ligase (Promega Corp.). The reaction was incubated overnight (~18 hours) at a temperature gradient of 0° C. to 18° C. The reaction was further incubated overnight at 12° C. The reaction was terminated by the addition of 75 μl of water and 10 μl of 3 M Na acetate, followed by incubation at 65° C. for 30 minutes. After incubation, the cDNA was extracted with phenol/chloroform and chloroform as described above and precipitated in the presence of 2.5 M ammonium acetate and 1.2 volume of isopropanol. Following centrifugation, the cDNA pellet was washed with 70% ethanol, air dried and resuspended in 89 μl water.

To facilitate the directional cloning of the cDNA into a lambda phage vector, the cDNA was digested with Not I, resulting in a cDNA having 5' Eco RI and 3' Not I cohesive ends. The Not I restriction site at the 3' end of the cDNA had been previously introduced through primer ZG6091 (SEQ ID NO: 7). Restriction enzyme digestion was carried out in a reaction containing 89 μl of cDNA described above, 10 μl of 6 mM Tris:HCl, 6 mM MgCl$_2$, 150 mM NaCl, 1 mM DTT (10× D buffer; Promega Corp., Madison, Wis.) and 1 μl of 12 U/μl Not I (Promega Corp.). Digestion was carried out at 37° C. for 1 hour. The reaction was terminated by serial phenol/chloroform and chloroform extractions. The cDNA was ethanol precipitated, washed with 70% ethanol, air dried and resuspended in 20 μl of 1× gel loading buffer (10 mM Tris:HCl, pH 8.0, 1 mM EDTA, 5% glycerol and 0.125% bromphenol blue).

The resuspended cDNA was heated to 65° C. for 5 minutes, cooled on ice and electrophoresed on a 0.8% low melt agarose gel (SEA PLAQUE GTG™ low melt agarose; FMC Corp.). Unincorporated adapters and cDNA below 1.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water (300 μl) approximately three times the volume of the gel slice was added to the tube, and the agarose was melted by heating to 65° C. for 15 minutes. Following equilibration of the sample to 42° C., 10 μl of 1 U/μl β-agarase I (New England Biolabs, Inc.) was added, and the mixture was incubated for 90 minutes to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA in the supernatant was ethanol precipitated, washed in 70% ethanol, air-dried and resuspended in 37 μl of water for the kinase reaction to phosphorylate the ligated Eco RI adapters.

To the 37 μl cDNA solution described above was added 10 μl 10× ligase buffer (Stratagene Cloning Systems), and the mixture was heated to 65° C. for 5 minutes. The mixture was cooled on ice, and 5 μl 10 mM ATP and 3 μl of 10 U/μl T4 polynucleotide kinase (Stratagene Cloning Systems) were added. The reaction was incubated at 37° C. for 45 minutes and was terminated by heating to 65° C. for 10 minutes followed by serial extractions with phenol/chloroform and chloroform. The phosphorylated cDNA was ethanol precipitated in the presence of 2.5 M ammonium acetate, washed with 70% ethanol, air dried and resuspended in 12.5 μl water. The concentration of the phosphorylated cDNA was estimated to be ~40 fmole/μl.

The resulting cDNA was cloned into the lambda phage vector λExCell™ (Pharmacia LKB Biotechnology Inc.), purchased predigested with Eco RI and Not I and dephosphorylated. Ligation of cDNA to vector was carried out in a reaction containing 2 μl of 20 fmole/μl prepared λExCell™ phage arms, 4 μl of water, 1 μl 10× ligase buffer (Promega Corp.), 2 μl of 40 fmole/μl cDNA and 1 μl of 15 U/μl T4 DNA ligase (Promega Corp.). Ligation was carried out at 4° C. for 48 hours. Approximately 50% of the ligation mixture was packaged into phage using GIGAPACK® II Gold packaging extract (Stratagene Cloning Systems) according to the directions of the vendor. The resulting cDNA library contained over 1.5×10⁷ independent recombinants with background levels of insertless phage of less than 1.5%.

A $^{32}$P-labeled human MPL-K receptor cDNA probe was used to isolate mouse MPL receptor cDNA from the mouse spleen cDNA phage library. The cDNA library was plated on SURE® strain of E. coli cells (Stratagene Cloning Systems) at a density of 40,000 to 50,000 PFU/150 mm diameter plate. Phage plaques from thirty-three plates were transferred onto nylon membranes (Hybond NTM; Amersham Corp., Arlington Heights, Ill.) and processed according to the directions of the manufacturer. The processed filters were baked for 2 hours at 80° C. in a vacuum oven followed by several washes at 70° C. in wash buffer (0.25× SSC, 0.25% SDS, 1 mM EDTA) and prehybridized overnight at 65° C. in hybridization solution (5× SSC, 5× Denhardt's solution, 0.1% SDS, 1 mN EDTA and 100 μg/ml heat denatured salmon sperm DNA) in a hybridization oven (model HB-2; Techne Inc., Princeton, N.J.). Following prehybridization, the hybridization solution was discarded and replaced with fresh hybridization solution containing approximately 2×10⁶ cpm/ml of $^{32}$P-labeled human MPL-K cDNA prepared by the use of a commercially available labeling kit (MEGAPRIME™ kit; Amersham Corp., Arlington Heights, Ill.). The probe was denatured at 98° C. for 5 minutes before being added to the hybridization solution. Hybridization was at 65° C. overnight. The filters were washed at 55° C. in wash buffer (0.25× SSC, 0.25% SDS, 1 mM EDTA) and were autoradiographed with intensifying screens for 4 days at −70° C. on XAR-5 film (Kodak Inc., Rochester, N.Y.). Employing the autoradiograph as template, agar plugs were recovered from regions of the plates corresponding to primary signals and were soaked in SM (0.1 M NaCl; 50 mM Tris:HCl, pH 7.5, 0.02% gelatin) to elute phage for plaque purification. Seven plaque-purified phages were isolated that carried inserts hybridizing to the human MPL-K receptor probe. The phagemids contained within the λExCell™ phage were recovered using the in vivo recombination system in accordance with the directions of the vendor. The identity of the cDNA inserts was confirmed by DNA sequencing.

The isolated clones encoded a protein exhibiting a high degree of sequence identity to human MPL-P receptor and to a recently reported mouse MPL receptor (Skoda et al., EMBO J. 12: 2645–2653, 1993). The seven clones fell into two classes differing from each other by three clones having a deletion of sequences encoding a stretch of 60 amino acid residues near the N-terminus. The cDNA encoding the protein without the deletion was referred to as mouse Type I MPL receptor cDNA. Type II receptor cDNA lacked sequences encoding Type I receptor residues 131 to 190 of SEQ ID NO: 17. In addition, Type I and II receptors differed from the reported mouse MPL receptor sequence (Skoda et al., ibid.) by the presence of a sequence encoding the amino acid residues Val-Arg-Thr-Ser-Pro-Ala-Gly-Glu (SEQ ID NO: 9) inserted after amino acid residue 222 and by a substitution of a glycine residue for serine at position 241 (positions refer to the Type I mouse receptor).

Type I and II mouse MPL receptor cDNAs were subcloned into the plasmid vector pHZ-1 for expression in mammalian cells. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator. To facilitate directional cloning into pHZ-1, a polymerase chain reaction employing appropriate primers was used to create an Eco RI site and a Xho I site upstream from the translation initiation codon and downstream from the translation termination codon, respectively. The polymerase chain reaction was carried out in a mixture containing 10 μl 10× ULTMA™ DNA polymerase buffer (Roche Molecular Systems, Inc., Branchburg, N.J.), 6 μl of 25 mM MgCl₂, 0.2 μl of a deoxynucleotide triphosphate solution containing 10 mM each of dATP, dGTP, dTTP and dCTP (Pharmacia LKB Biotechnology Inc.), 2.5 μl of 20 pmole/μl primer ZC6603 (SEQ ID NO: 8), 2.5 μl of 20 pmole/μl primer ZC5762 (SEQ ID NO: 5), 32.8 μl of water, 1 μl of an early log phase bacterial culture harboring either a Type I or a Type II mouse MPL receptor plasmid and 1 μl of 6 U/μl DNA polymerase (ULTMA™ polymerase; Roche Molecular Systems, Inc., Branchburg, N.J.). AmpliWax™ (Roche Molecular Systems, Inc.) was employed in the reaction according to the directions of the vendor. The polymerase chain reaction was run for 25 cycles (1 minute at 95° C., 1 minute at 55° C. and 3 minutes at 72° C.) followed by a 10 minute incubation at 72° C. The amplified products were serially extracted with phenol/chloroform and chloroform, then ethanol precipitated in the presence of 6 μg glycogen carrier and 2.5 M ammonium acetate. The pellets were resuspended in 87 μl of water to which was added 10 μl of 10× H buffer (Boehringer Mannheim Corp.), 2 μl of 10 U/μl Eco RI (Boehringer Mannheim) and 1 μl of 40 U/μl Xho I (Boehringer Mannheim Corp.). Digestion was carried out at 37° C. for 1 hour. The reaction was terminated by heating to 65° C. for 15 minutes and chromatographed through a 400 pore size gel filtration column (CHROMA SPIN+TE-400™; Clontech Laboratories Inc.).

The isolated receptor inserts described above were ligated into Eco RI and Xho I digested and dephosphorylated pHZ-1 vector. The ligation reaction contained 1 μl of 50 ng/μl prepared pHZ-1 vector, 5 μl of 5 ng/μl cDNA insert, 2 μl of 10× ligase buffer (Promega Corp.), 11.75 μl water and 0.25 μl of 4 U/μl T4 DNA ligase (Stratagene Cloning Systems). Ligation was carried out at 10° C. overnight. The ligated DNAs were transfected into E. coli (MAX EFFICIENCY DH10B™ competent cells; GIBCO BRL) in accordance with the vendor's directions. The validity of Type I and Type II mouse MPL and human MPL-P receptor inserts in pHZ-1 was confirmed by DNA sequencing. The resulting plasmids pSLmpl-8 and pSLmpl-9 carried the mouse Type II and Type I MPL receptor cDNAs, respectively. Plasmid pSLmpl-44 carried the human MPL-P cDNA insert.

EXAMPLE III

Construction of BaF3 Cell Lines Expressing MPL Receptors

BaF3, an interleukin-3 dependent pre-lymphoid cell line derived from murine bone marrow (Palacios and Steinmetz, *Cell* 41: 727–734, 1985; Mathey-Prevot et al., *Mol. Cell. Biol.* 6: 4133–4135, 1986), was maintained in complete media (RPMI 1640 medium (JRH Bioscience Inc., Lenexa, Kans.) supplemented with 10% heat-inactivated fetal calf serum, 4% conditioned media from cultured WEHI-3 cells (Becton Dickinson Labware, Bedford, MA), 2 mM L-glutamine, 2-mercaptoethanol (1:280,000 final conc.) and PSN antibiotics (GIBCO BRL)). Cesium chloride purified plasmids pSLmpl-8, pSLmpl-9 and pSLmpl-44 were linearized at the Nde I site prior to electroporation into BaF3 cells. BaF3 cells for electroporation were washed once in RPMI 1640 media and resuspended in RPMI 1640 media at a cell density of $10^7$ cells/ml. One ml of resuspended BaF3 cells was mixed with 30 μg of each of the linearized plasmid DNAs and transferred to separate disposable electroporation chambers (GIBCO BRL). Following a 15 minute incubation at room temperature the cells were given two serial shocks (800 μFad/300 V.; 1180 μFad/300 V.) delivered by an electroporation apparatus (CELL-PORATOR™; GIBCO BRL). After a 5 minute recovery time, the electroporated cells were transferred to 10 ml of complete media and placed in an incubator for 15–24 hours (37° C., 5% $CO_2$). The cells were then spun down and resuspended in 10 ml of complete media containing 1600 μ/ml G418 and plated at limiting dilutions in 96-well tissue culture plates to isolate G418-resistant clones. Expression of MPL receptors in G418-resistant BaF3 clones was inferred by Northern blot analysis of BaF3 mRNA for the presence of MPL receptor transcript. A cell line designated BaF3/MPLR1.1 was found to express high levels of Type I mouse MPL receptor mRNA and was used for subsequent assay for MPL ligand activity in conditioned media of transfected BHK 570 cells. A BaF3 cell line expressing Type II receptor mRNA was designated as BaF3/MPLR2.

EXAMPLE IV

Production of Soluble Mouse MPL Receptor

A mammalian expression plasmid encoding soluble mouse Type I MPL receptor (pLDmpl-53) was produced by combining DNA segments from pSLmpl-9, a mammalian expression plasmid containing the cDNA encoding full-length mouse Type I MPL receptor described above, with a DNA segment from pSLmpl-26, an expression plasmid constructed to produce the soluble mouse Type I MPL receptor in bacteria.

A cDNA segment encoding mouse Type I MPL soluble receptor was isolated by PCR employing primers ZC6704 (SEQ ID NO: 10) and ZC6703 (SEQ ID NO: 11) using full-length receptor plasmid pSLmpl-9 as template. To facilitate directional cloning, primers ZC6704 and ZC6703 incorporated Eco RI and Xho I restriction sites at their respective 5' ends. Primer ZC6703 also encoded an inframe consensus target sequence for protein kinase to enable in vitro labeling of the purified soluble receptor with $^{32}$P γ-ATP (Li et al., *Proc. Natl. Acad. Sci. U.S.A.* 86: 558–562, 1989). The PCR was carried out in a mixture containing 10 μl 10× ULTMA™ DNA polymerase buffer (Roche Molecular Systems, Inc.), 6 μl of 25 MM $MgCl_2$, 0.2 μl of a deoxynucleotide triphosphate solution containing 10 mM each of DATP, dGTP, dTTP and dCTP (Pharmacia LKB Biotechnology Inc.), 11 μl of 4.55 pmole/μl primer ZC6704 (SEQ ID NO: 10), 21 μl of 2.43 pmole/μl primer ZC6703 (SEQ ID NO: 11), 50.3 μl of water, 1 μl 50 ng/μl Hind III and Xba I digested pSLmpl-9 and 1 μl of 6 U/μl ULTMA™ DNA polymerase (Roche Molecular Systems, Inc.). AmpliWax™ (Roche Molecular Systems, Inc.) was employed in the reaction according to the directions of the vendor. The polymerase chain reaction was run for 3 cycles (1 minute at 95° C., 1 minute at 50° C. and 2 minutes at 72° C.) followed by 11 cycles at increased hybridization stringency (1 minute at 95° C., 30 seconds at 55° C. and 2 minutes at 72° C.) followed by a 10 minute incubation at 72° C. The amplified product was serially extracted with phenol/chloroform and chloroform followed by chromatography through a 400 pore size gel filtration column (Clontech Laboratories, Inc.). The PCR product was ethanol precipitated in the presence of 20 μg glycogen carrier and 2.5 M ammonium acetate. The pellet was resuspended in 32 μl of water. To 16 μl of the resuspended PCR product was added 2 μl 10× H buffer (Boehringer Mannheim Corp.), 1 μl of 10 U/μl Eco RI (Boehringer Mannheim Corp.) and 1 μl of 40 U/μl Xho I (Boehringer Mannheim Corp.). Digestion was carried out at 37° C. for 1 hour. Digestion was terminated by heating to 65° C. for 15 minutes and was purified on a 0.7% low-melt agarose gel. Fragment recovery from low-melt agarose was done by digestion of the gel matrix with β-agarase I (New England Biolabs).

The resulting PCR product encoded the N-terminal extracellular domain of mouse Type I MPL receptor (residues 27 to 480 of SEQ ID NO: 17). In the absence of the putative receptor trans-membrane domain (residues 483 to 504 of SEQ ID NO: 17) the expressed protein is expected to be secreted in the presence of a suitable signal peptide. A mouse Type II soluble MPL receptor encoding cDNA was obtained using the PCR conditions described above except that pSLmpl-8 was used as template. The validity of both receptor fragments was confirmed by DNA sequencing.

The soluble mouse Type I and Type II MPL receptor encoding DNA fragments were cloned into Eco RI and Xho I digested vector pOmpA2-5 to yield pSLmpl-26 and pSLmpl-27, respectively. Plasmid pOmpA2-5 is a modification of pOmpA2 (Ghrayab et al., *EMBO J.* 3: 2437–2442, 1984), a bacterial expression vector designed to target the recombinant protein to the periplasmic space. pOmpA2-5 was constructed by replacement of a 13 bp sequence between the Eco RI and Bam HI sites of pOmpA2 with a synthetic 42 bp sequence. The sequence was created by annealing of two 42 nucleotide complementary oligonucleotides (ZC6707, SEQ ID NO: 12; ZC6706, SEQ ID NO: 13), which when base paired formed Eco RI and Bam HI cohesive ends, facilitating directional cloning into Eco RI and Bam HI digested pOmpA2. Within the inserted sequence is an Xho I site inframed with respect to a bacterial leader sequence and to the mouse MPL soluble receptor encoding cDNAs described above, as well as an inframe tract of 6 histidine codons located 3' of the Xho I site to enable the recombinant protein to be purified by metal chelation affinity chromatography (Houchuli et al., *Bio/Technol.* 6: 1321–1325, 1988). Following the sequence encoding the histidine tract was an inframe termination codon. The validity of the pOmpA2–5, pSLmpl-26 and pSLmpl-27 was confirmed by DNA sequencing.

pLDmpl-53, a mammalian expression plasmid producing soluble mouse Type I MPL receptor, was constructed by combining DNA segments from pSLmpl-9 and pSLmpl-26 into expression vector pHZ-200 (pHZ-1 in which a dihydrofolate reductase sequence was substituted for the neomycin resistance gene). The 1164 bp Eco RI/Bam HI cDNA fragment from pSLmpl-9 replaced the mammalian signal sequence deleted during the construction of bacterial expression plasmid pSLmpl-26. The 416 bp Bam HI fragment from pSLmpl-26 supplied the coding sequence for the carboxyterminal portion of the soluble MPL receptor, the kinase labeling domain, the poly-histidine tract and the translation terminator. The two fragments were gel purified and cloned into the Eco RI/Bam HI sites of pBluescript® KS+ (Stratagene Cloning Systems) to yield plasmid pBS8.76LD-5. Correct orientation of the the 416 bp pSLmpl-26 derived Bam HI fragment with respect to the 1164 bp pSLmpl-9 derived Eco RI/Bam HI fragment in pBS8.76LD-5 was determined by PCR using primers ZC 6603 (SEQ ID NO: 8) and ZC 6703 (SEQ ID NO: 11). The Xba I site within the poly-linker sequence of pBS8.76LD-5 enabled the reconstituted receptor cDNA to be excised as a 1.5 kb Eco RI/Xba I fragment for cloning into pHZ-200 following digestion of the vector with Eco RI and Xba I. The resulting mammalian expression plasmid, pLDmpl-53, was prepared in large scale for transfection into BHK cells.

Twenty micrograms of purified pLDmpl-53 plasmid was transfected into BHK 570 cells using the calcium phosphate precipitation method. After 5 hours, the cells were shocked with 15% glycerol for 3 minutes to facilitate uptake of DNA. Fresh growth media was added overnight. The following day the cells were split at various dilutions, and selection media containing 1 $\mu$M methotrexate was added. After approximately two weeks, discrete, methotrexate-resistant colonies were visible. Resistant colonies were either pooled or maintained as distinct clones. Spent media from the pooled colonies was immediately tested for presence of soluble MPL receptor protein.

Soluble MPL receptor protein was isolated through the interaction of the poly-histidine tract present on the carboxyterminal of the protein with a metal chelation resin containing immobilized $Ni^{2+}$ (HIS-BIND™; Novagen, Madison, Wis.). Serum-free spent culture media from the pLDmpl-53 pool was passed over the resin, and bound protein was eluted with imidazole. SDS-PAGE analysis revealed a single band at ~67 kDa. This protein was subjected to N-terminal amino acid analysis and confirmed to be mouse MPL receptor.

Soluble mouse MPL receptor was purified from a pool of BHK transfectants, which had been transfected with the soluble mouse Type I MPL receptor expressing plasmid pLDmpl-53. The purified soluble receptor was immobilized on CNBr-activated SEPHAROSE™ 4B (Pharmacia LKB Biotechnology, Inc.) matrix essentially as directed by the manufacturer and used for affinity purification of the MPL activity in conditioned media of 24-11-5 cells. The affinity matrix was packed in a XK16 column (Pharmacia LKB Biotechnology Inc.). Conditioned media from 24-11-5 cells were concentrated on a 10 Kd cut off hollow fiber membrane (A/G Technology Corp., Needham, Mass.) and loaded onto the bottom of the MPL receptor affinity column at a flow rate of 1 ml/minute. The column was washed with phosphate buffed saline (PBS) containing 0.5 M NaCl and 0.01% sodium azide. MPL activity was eluted from the column with 3M potassium thiocyanate (Sigma Chemical Company, St. Louis, Mo.) at a flow rate of 0.5 ml/minute. Potassium thiocyanate was removed by dialysis against PBS. Active fractions were identified by MTT proliferation assay (disclosed in Example VII).

EXAMPLE V

Isolation and Characterization of a MPL Receptor Ligand Expressina Cell Line

BaF3/MPLR1.1 cells are IL-3 dependent cells expressing a stably transfected Type I mouse MPL receptor. A mutagenesis and selection scheme was devised to isolate cell lines expressing the MPL receptor ligand by mutagenizing BaF3/MPLR1.1 cells, and selecting for autocrine growth in the absence of exogenous IL-3.

Approximately $1.2 \times 10^6$ BaF3/MPLR1.1 cells were pelleted and washed with GM (RPMI 1640 media supplemented with 2-mercaptoethanol (1:240,000 final concentration), 2 mM L-glutamine, 110 $\mu$g/ml sodium pyruvate, 50 $\mu$g/ml G418 and 10% heat inactivated fetal bovine serum). The cells were resuspended in 2 ml of GM containing 0.15% (v/v) of the mutagen 2-ethylmethanesulfonate (EMS) and incubated for 2 hours at 37° C. After incubation, the cells were washed once in PBS and once in GM and plated onto 10 cm plates at density of approximately 40,000 cells/ml in GM supplemented with 5% WEHI-3 conditioned media (Becton Dickinson Labware, Bedford, Mass.) as a source of IL-3. The cells were allowed a recovery period of seven days incubated at 37° C. under 5% $CO_2$ before selection for IL-3 independent growth. Following the recovery period, the culture was dense with viable cells. The cells were washed with GM and were cultured in GM in the absence of WEHI-3 conditioned media. After eleven days of selection, small numbers of viable cells were observed. The viable cell density of the IL-3 independent culture was estimated to be 250 cells/ml. One ml of the IL-3 independent culture was plated onto each of 19 wells of a 24-well culture plate for further characterization.

Conditioned media from the above IL-3 growth independent BaF3/MPLR1.1 cells were assayed for proliferative activity on BaF3/MPLR cells. Conditioned media from all nineteen IL-3 growth independent pools were found to have activity in the MTT proliferatation assay (disclosed in Example VII). The positive media were reassayed for proliferative activity in the presence of 2 µg/ml rat anti-mouse IL-3, anti-mouse IL-4 or in the presence of both neutralizing antibodies (Pharmingen, San Diego, Calif.) to identify IL-3 growth independent mutants expressing those cytokines. (In a previous experiment, it was found that BaF3 cells also responded to IL-4.) Only conditioned medium from cells from plate #11 (designated "24-11" cells) was found to have activity that was not neutralized by IL-3 or IL-4 antibodies.

The mutagenesis and selection scheme described above was applied to five other BaF3/MPLR1 clones (BaF3/MPLR1 clones # 4, 9, 12, 15 and 18, designated as BaF3/MPLR1.4, 0.9, 0.12, 0.15 and 0.18, respectively). Seventeen isolates were found to have conditioned media which stimulated proliferation of BaF3/MPLR1 cells. Activity of all the media was found to be neutralized by anti-IL-3 or IL-4 antibodies alone or in combination. These clones were not characterized further.

The proliferative activity of conditioned media from the 24-11 pool was characterized in detail. The 24-11 pool was subdivided into nineteen subpools, and conditioned media were retested for activity. All nineteen subpools (i.e. 24-11-1 thru 24-11-19) stimulated proliferation of IL-3 growth dependent BaF3/MPLR1 cells in the absence of exogenous IL-3. The activity was not inhibited by IL-3 or IL-4 neutralizing antibodies or by a combination of both antibodies.

Two experiments were performed to determine the specificity of the 24-11 activity. The conditioned media were assayed for proliferative activity on control BaF3 cells that do not express the MPL receptor. In the absence of exogenous IL-3, proliferation of control BaF3 cells was not observed in the conditioned media from any of the nineteen 24-11 subpools. In a second experiment, proliferative activity was assayed for inhibition by purified soluble MPL receptor. BaF3/MPLR1 cells were cultured in GM media supplemented with 50% 24-11 conditioned media. To each sample was added Type I mouse soluble MPL receptor to a final concentration of 0.0, 0.625, 1.25, 2.5 or 5.0 µg/ml. The results were scored 4 days later by MTT cell proliferation assay. The proliferative activity of the 24-11 conditioned media was completely blocked at 0.625 to 1.25 µg/ml soluble MPL receptor. Soluble receptor concentrations that completely inhibited activity had no effect on IL-3 or IL-4 stimulation of BaF3/MPLR1 cells. The results indicated that soluble MPL receptor competed for the stimulatory activity of 24-11 media and were consistent with the hypothesis that 24-11 cells expressed the MPL receptor ligand.

Clones derived from 24-11 cells were isolated by plating at limiting dilutions. One clone, designated 24-11-5 #3, showed a high level of proliferative activity in its conditioned media relative to the 24-11 pool. The proliferative activity was found to be equal to a 1:2000 dilution of conditioned media from WEHI-3 cells (Becton Dickinson Labware).

EXAMPLE VI

Construction of 24-11-5#3 cDNA Library

Total RNA was prepared from ~2.7×10$^8$ 24-11-5 #3 cells using guanidine isothiocyanate followed by CsCl centrifugation (Chirgwin et al., ibid.). Poly(A)$^+$ RNA was isolated using an OLIGOTEX-dT-mRNA isolation kit (Qiagen Inc., Chatsworth, Calif.) following the manufacturer's instructions.

First strand cDNA from 24-11-5#3 cells was synthesized in 4 separate parallel reactions. Each reaction contained 7 µl of poly d(T)-selected poly(A)$^+$ 24-11-5#3 RNA at a concentration of 1.6 µg/µl and 2.5 µl of 20 pmole/µl first strand primer ZC6172 (SEQ ID NO: 14) containing an Xho I restriction site. The mixture was heated at 65° C. for 4 minutes and cooled by chilling on ice. First strand cDNA synthesis was initiated by the addition of 8 µl of first strand buffer (5× SUPERSCRIPT™ buffer; GIBCO BRL), 4 µl of 100 mM dithiothreitol and 2 µl of a deoxynucleotide triphosphate solution containing 10 mM each of DATP, dGTP, dTTP and 5-methyl-dCTP (Pharmacia LKB Biotechnology Inc.) to the RNA-primer mixture. The reaction mixture was incubated at 45° C. for 4 minutes followed by the addition of 10 µl of 200 U/µl RNase H_reverse transcriptase (GIBCO BRL). The efficiency of the first strand synthesis was analyzed in a parallel reaction by the addition of 10 µCi of $^{32}$P-αdCTP to a 10 µl aliquot from one of the reaction mixtures to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (Clontech Laboratories). The unlabeled first strand reactions were pooled, and unincorporated nucleotides were removed by twice precipitating the cDNA in the presence of 32 µg of glycogen carrier, 2.5 M ammonium acetate and 2.5 volume ethanol. The unlabeled cDNA was resuspended in 144 µl water for use in second strand synthesis. The length of labeled first strand cDNA was determined by agarose gel electrophoresis.

Second strand synthesis was performed on the first strand cDNA under conditions that promoted first strand priming of second strand synthesis resulting in DNA hairpin formation. Three separate parallel second strand reactions were performed. Each second strand reaction contained 48 µl of the unlabeled first strand cDNA, 16.5 µl of water, 20 µl of 5× polymerase I buffer (100 mM Tris: HCl, pH 7.4, 500 mM KCl, 25 mM MgCl$_2$, 50 mM (NH$_4$)$_2$SO$_4$), 1 µl of 100 mM dithiothreitol, 1 µl of a solution containing 10 mM of each deoxynucleotide triphosphate, 3 µl of 5 mM β-NAD, 1 µl of 3 U/µl E. coli DNA ligase (New England Biolabs Inc.) and 5 µl of 10 U/µl E. coli DNA polymerase I (Amersham Corp.). The reaction was assembled at room temperature and was incubated at room temperature for 5 minutes followed by the addition of 1.5 µl of 2 U/µl RNase H (GIBCO BRL). A 10 µl aliquot from one of the second strand synthesis reactions was labeled by the addition of 10 µCi $^{32}$P-αdCTP to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories) before analysis by agarose gel electrophoresis. The unlabeled reactions were pooled and extracted with phenol/chloroform and chloroform followed by ethanol precipitation in the presence of 2.5 M ammonium acetate.

The single-stranded DNA of the hairpin structure was cleaved using mung bean nuclease. The reaction mixture contained 100 µl of second strand cDNA, 20 µl of 10× mung bean nuclease buffer (Stratagene Cloning Systems), 16 µl of 100 mM dithiothreitol, 48 µl of water, 10 µl of mung bean nuclease dilution buffer (Stratagene Cloning Systems) and 6

μl of 50 U/μl mung bean nuclease (Promega Corp.). The reaction was incubated at 37° C. for 30 minutes. The reaction was terminated by the addition of 20 μl of 1 M Tris:HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 188 μl of water, was mixed with 50 μl 5× T4 DNA polymerase buffer (250 mM Tris:HCl, pH 8.0, 250 mM KCl, 25 mM MgCl$_2$), 3 μl 0.1 M dithiothreitol, 4 μl of a solution containing 10 mM of each deoxynucleotide triphosphate and 5 μl of 1 U/μl T4 DNA polymerase (Boehringer Mannheim Corp.). After an incubation of 30 minutes at 15° C., the reaction was terminated by the addition of 10 μl of 0.5 M EDTA followed by serial phenol/chloroform and chloroform extractions as described above. The DNA was chromatographed through a 400 pore size gel filtration column (Clontech Laboratories Inc.) to remove trace levels of protein and to remove short cDNAs less than ~400 bp in length. The DNA was ethanol precipitated in the presence of 10 μg glycogen carrier and 2.5 M ammonium acetate and was resuspended 15 μl of water. Based on the incorporation of $^{32}$P-αdCTP, the yield of cDNA was estimated to be ~8 μg from a starting mRNA template of 40 μg.

Eco RI adapters were ligated onto the 5' ends of the cDNA described above to enable cloning into an expression vector. A 10 μl aliquot of cDNA (~5 μg) and 21 μl of 65 pmole/μl of Eco RI adapter (Pharmacia LKB Biotechnology Inc.) were mixed with 4 μl 10× ligase buffer (Promega Corp.), 3 μl of 10 mM ATP and 3 μl of 15 U/μl T4 DNA ligase (Promega Corp.). The reaction was incubated overnight (~48 hours) at 9° C. The reaction was terminated by the addition of 140 μl of water, 20 μl of 10× H buffer (Boehringer Mannheim Corp.) and incubation at 65° C. for 40 minutes. After incubation, the cDNA was extracted with phenol/chloroform and chloroform as described above and precipitated in the presence of 2.5 M ammonium acetate and 1.2 volume of isopropanol. Following centrifugation, the cDNA pellet was washed with 70% ethanol, air dried and resuspended in 89 μl water.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6172 primer (SEQ ID NO: 14). Restriction enzyme digestion was carried out in a reaction mixture containing 89 μl of cDNA described above, 10 μl of 10× H buffer (Promega Corp.) and 1.5 μl of 40 U/μl Xho I (Boehringer Mannheim Corp.). Digestion was carried out at 37° C. for 1 hour. The reaction was terminated by serial phenol/chloroform and chloroform extractions and chromatography through a 400 pore size gel filtration column (Clontech Laboratories Inc.).

The cDNA was ethanol precipitated, washed with 0% ethanol, air dried and resuspended in 20 μl of 1× gel loading buffer (10 mM Tris:HCl, pH 8.0, 1 mM EDTA, 5% glycerol and 0.125% bromphenol blue). The resuspended cDNA was heated to 65° C. for 5 minutes, cooled on ice and electrophoresed on a 0.8% low melt agarose gel (SEA PLAQUE GTG™ low melt agarose; FMC Corp.). The contaminating adapters and cDNA below 0.5 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) was added to the tube, and the agarose was melted by heating to 65° C. for 15 minutes. Following equilibration of the sample to 45° C., 5 μl of 1 U/μl β-agarase I (New England Biolabs, Inc.) was added, and the mixture was incubated for 90 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose followed by chromatography through a 400 pore size gel filtration column (Clontech Laboratories). The cDNA was ethanol precipitated, washed in 70% ethanol, air-dried and resuspended in 70 μl water for the kinase reaction to phosphorylate the ligated Eco RI adapters.

To the 70 μl cDNA solution was added 10 μl 10× ligase buffer (Stratagene Cloning Systems), and the mixture was heated to 65° C. for 5 minutes. The mixture was cooled on ice, and 16 μl 10 mM ATP and 4 μl of 10 U/μl T4 polynucleotide kinase (Stratagene Cloning Systems) were added. The reaction mixture was incubated at 37° C. for 1 hour and was terminated by heating to 65° C. for 10 minutes followed by serial extractions with phenol/chloroform and chloroform. The phosphorylated cDNA was ethanol precipitated in the presence of 2.5 M ammonium acetate, washed with 70% ethanol, air dried and resuspended in 10 μl of water. The concentration of the phosphorylated cDNA was estimated to be ~40 fmole/μl.

The pDX mammalian expression vector (disclosed in U.S. Pat. No. 4,959,318) (Figure) was modified to accept 24-11-5#3 cDNA that had been synthesized with Eco RI-Xho I ends. An endogenous Sal I site on pDX was eliminated by digesting the plasmid with Sal I and recircularizing the plasmid following blunting of the Sal I cohesive ends with T4 DNA polymerase. The recircularized plasmid was digested with Eco RI and to it was ligated a short polylinker sequence consisting of two complementary oligonucleotides, ZC6936 (SEQ ID NO: 15) and ZC6937 (SEQ ID NO: 16), to yield plasmid pDX.ES. The introduced polylinker sequence on pDX.ES contained Eco RI and Sal I sites to facilitate directional cloning of 24-11-5 cDNA synthesized with Eco RI-Xho I ends.

A plasmid cDNA library was prepared by ligating Eco RI-Xho I 24-11-5 cDNA into Eco RI/Sal I digested pDX.ES. The ligation mixture was electroporated into *E. coli* (ELECTROMAX DH10B™ competent cells; GIBCO BRL, Gaithersburg, Md.) using a gene pulser/pulse controller and 0.2 cm cuvette (Bio-Rad Laboratories, Hercules, Calif.) employing a 0.2 KV, 400 ohm and 25 μFAD. The cells were diluted to 1.5 ml in Luria broth and incubated at 37° C. for 45 minutes followed by the addition of 0.75 ml of 50% glycerol. The transfected cells were aliquotted and stored at −70° C. until use. Eighty fmoles of cDNA gave rise to over 700,000 independent recombinant plasmids.

EXAMPLE VII

Expression Screening of 24-11-5 cDNA Library for MPL Activity

The 24-11-5#3 cDNA library was plated onto approximately two thousand 10 cm diameter Luria broth agar plates supplemented with 100 μg/ml ampicillin. The plating density was between 200 and 250 bacterial colonies per plate. Plasmid DNA for transfection into BHK 570 cells was prepared from each bacterial plate using MAGIC MINI- PREPS™ DNA purification resin (Promega Corp.), according to the manufacturer's instruction. Plasmid DNAs were stored at -20° C. until transfection into BHK 570 cells.

Plasmid pools of 24-11-5#3 cDNA, each containing approximately 200 to 250 cDNA clones, were transfected into BHK 570 cells using a 3:1 liposome formulation of 2,3-dioleyloxy-N-[2(sperminecarboxyamido)ethyl]-N,N-dimethyl-1-propanaminiumtrifluoroacetate and dioleoly-phosphatidylethanolamine in water (LIPOFECTAMINE™; GIBCO BRL). Twenty μl of 30 ng/μl DNA was added to 20 μl of a 1:10 dilution of LIPOFECTAMINE™ solution and incubated at room temperature for 30 minutes. Following the incubation, 160 μl of serum-free media (Hams F12: Dulbeccos MEM (1:1) suplemented with 2 mM L-glutamine, 0.11 mg/ml sodium pyruvate, 5 μg/ml insulin, 5 μg/ml fetuin, 10 μg/ml transferrin, 2 ng/ml selenium IV oxide and 25 mM HEPES buffer) were added to the DNA/LIPOFECTAMINE™ mixture and transferred to a 24 well microtiter plate containing ~100,000 BHK 570 cells. The cells were incubated at 37° C. under 5% $CO_2$ for 4 hours, after which was added 200 μl of BHK Growth Media (Dulbecco's modified Eagles's media suplemented with 2 mM L-glutamine, 0.11 mg/ml sodium pyruvate, 5% heat inactivated fetal calf serum and 100× PSN antibiotics (GIBCO BRL)). The cells were incubated for 16 hours. The media was removed and replaced with 0.5 ml of fresh BHK Growth Media, which was conditioned for 48 hours before being assayed for MPL activity.

A cell proliferation assay was used to detect the presence of MPL activity in conditioned media of library transfected BHK 570 cells. One hundred μl of conditioned media was added to 100 μl of $10^6$/ml washed BaF3/MPLR1.1 cells in RPMI 1640 media (JRH Bioscience Inc., Lenexa, KS) supplemented with 2 mM L-glutamine, PSN antibiotics (GIBCO BRL), 0.00036% 2-mercaptoethanol and 10% heat inactivated fetal calf serum. The assay cells were incubated for 3 days at 37° C. under 5% $CO_2$ before assaying for proliferation.

Cell proliferation in the presence of MPL was quantified using a colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, 1983). Twenty μl of a 10 mg/ml solution of MTT (Polyscience, Inc., Warrington, Pa.) was added to 100 μl of BaF3/MPLR1.1 assay cells, and the cells were incubated at 37° C. After 4 hours, 200 μl of 0.04 N HCl in isopropanol was added, the solution was mixed, and the absorbance of the sample was read at 570 nm on a model EL320 ELISA reader (Bio-Tek Instruments Inc., Highland Park, Vt.).

One plasmid pool found to be positive, designated T1081, was transfected into BHK 570 cells. Supernatant from the transfectants gave a positive signal in the MTT proliferation assay. PCR and antibody neutralization experiments demonstrated that the activity was not due to IL-3 or IL-4.

Plasmids from the positive pool were used to transform *E. coli* DH10B, and cells were plated (42 plates with approximately 15–20 colonies per plate, 10 plates with approximately 90 colonies per plate and 8 plates with approximately 250 colonies per plate). A replica of each plate was made and stored at 4° C. The colonies on the original plates were scraped and allowed to outgrow in liquid culture for several more hours, then DNA was prepared.

The plasmid DNA from the sub-pools was transfected into BHK 570 cells, and cell supernatants were collected and assayed as above. After approximately two hours, one sub-pool (#22) was scored as positive by microscopic examination (elongated cell shape). Several hours later two additional sub-pools (#19 and #28) were also scored positive. Remaining supernatants from each positive sub-pool were assayed against the control BaF3 cells and found to have no activity. In addition, the activity from the three positive sub-pools was found to be inhibited by the soluble Type I MPL receptor.

The replica plates from the three positive sub-pools were allowed to grow for several hours, then individual colonies were picked and used to innoculate 3-ml cultures. The cultures were grown approximately 8 hours at 37° C., then DNA was prepared by the miniprep method as described above. Plasmid DNA was transfected into BHK 570 cells, and supernatants were harvested approximately 10 hours later and assayed for activity. After one hour, one clone (designated T1081-19-215, corresponding to sub-pool #19) was scored positive. This clone was restreaked for single colonies. DNA was prepared from twelve colonies and transfected into BHK 570 cells. All twelve transfectants were later scored positive in the assay. DNA from one of the twelve positive colonies was transformed into *E. coli* DH5α. The plasmid was designated pZGmpl-1081. This transformant has been deposited on Feb. 14, 1994 with American Type Culture Collection, 12301 Parklawn Drive, Rockville, Md. under accession number 69566.

The nucleotide sequence of the cDNA encoding the hematopoietic protein (thrombopoietin) was determined (SEQ ID NO: 1). Analysis of the encoded amino acid sequence (SEQ ID NO: 2) indicated that the amino terminus of the mature protein is at amino acid residue 45. Two methionine codons, at positions 105 and 174 of SEQ ID NO: 1, appear to be initiation codons, with the major site of initiation expected to be at position 174.

EXAMPLE VIII

Stimulation of Granulocyte/Macrophaae Colony Formation

Marrow was harvested from femurs and tibias of a female CD-1 post-pregnant mouse into 25 ml of CATCH buffer (99 mg theophylline, 0.75 g sodium citrate, 75 mg adenosine, 20 ml of 10× Hank's balanced saline solution $Ca^{++}$ $Mg^{++}$-free, per 200 ml in $dH_2O$; pH 7.4). Cells were suspended into single cell suspension by pipeting with a 25 ml pipet. The volume was brought up to 50 ml with CATCH buffer, and the cells were pelleted at 1000 rpm for 7 minutes. The pellet was resuspended in 25 ml CATCH buffer and incubated in a T75 tissue culture flask for a first round of plastic adherence at 37° C. or 2 hours. Non-adherent cells were harvested by centrifugation at 1000 rpm for 7 minutes to pellet cells. The pellet was resuspended in 15 ml alpha-MEM+10% FBS (+L-glutamine, NaPyruvate, and PSN antibiotics) and incubated in a T75 flask for a second round of plastic adherence as described above for the first round. Following the final centrifugation and resuspension, the cells were counted. One-half ml of cells at 576,000 cells/ml was plated into 24-well tissue culture plates, together with sample media from control BHK cells or with conditioned media from BHK cells transfected with pZGmpl-1081. After three days incubation at 37° C., the cells were harvested and stained as described below.

One hundred fifty ll of cells were harvested from the control well treated with standard conditioned medium. 50 μl of cells were harvested from the well treated with conditioned medium from BHK cells transfected with pZGmpl-1081. These samples were spun, and standard microscope slides were prepared.

The slides were fixed in 100% methanol, then flooded with 1:1 Wright's (0.5 g Wright stain in 300 ml methanol)/ $H_2O$ for 6 minutes, washed with water, and dried. Slides were then flooded with Giemsa stain (Sigma Chemical Corp.) in Sorensen buffer (2.28 g $KH_2PO_4$/2.38 g $NaPO_4$ in 250 ml $H_2O$), washed with water, and dried.

After adjusting for the volumes used, the BHK/pZGmpl-1081 medium sample contained 120 megakaryocytes per 150 μl volume as compared to 9 megakaryocytes per 150 μl volume of control medium. In addition, the megakaryocytes in the treated experimental sample were observed microscopically to be significantly larger in size than control cells and to have significantly higher staining for polynuclei content.

Conditioned media from the mutant BaF3/MPLR1.1 line 24-11-5 #3 was collected in the absence of serum and concentrated 20-fold on a 10Kd cut-off Amicon Inc. (Beverly, Mass.) filtration device. Marrow was harvested from mouse femurs and suspended in Iscove's Modified Dulbecco's Media (GIBCO BRL)+15% fetal calf serum (FCS). Following suspension, nucleated cells were counted and plated at 75,000 cells/ml with 0.9 ml/plate in medium adjusted to contain 0.9% methylcellulose, 15% FCS, 10% BSA, and 0.6% PSN (semi-solid medium) in 1 ml tissue culture plates. Various conditioned medium and control samples were added to bring the total volume to 1 ml. Plates were incubated at 37° C./5% $CO_2$ for 6 days and then examined microscopically for counts of granulocyte/macrophage (GM) colonies. Plates incubated in the presence of the 24-11-5 #3 conditioned medium were observed to have weak GMCSF-like activity, producing a colony count of 25, compared with a count of zero for the negative control sample, and a count of 130 for a plate stimulated with a positive control (pokeweed mitogen spleen conditioned medium (PWMSCM); prepared by incubating minced mouse spleen for one week in the presence of pokeweed mitogen (obtained from Boehringer Mannheim, Indianapolis, Ind.)+2 units/ml erythropoietin)

EXAMPLE IX

Receptor Affinity Precipitation 150-mm tissue culture plates containing transfected BHK cells producing TPO or normal BHK cells were labeled for 18 hours with 10 ml of Dulbecco's MEM without methoinine containing 2mM L-glutamine, antibiotics and 200 μCi of $^{35}$S-Express (Amersham, Arlington Heights, Ill.).

After the overnight incubation the spent media were collected and concentrated 15 times using a Centriprep-10™ concentrator (Amicon, Inc.). The resulting 0.7 ml of concentrated supernatant was mixed with 75 μl of poly-histidine tailed soluble MPL receptor which had been linked to nickel-Sepharose (Qiagen Inc., Chatsworth, Calif.) as directed by the supplier. The mixture was incubated for two hours on ice, while shaking.

The cells were washed once with PBS, then lysed with 1 ml of RIP A buffer (10 mM Tris, pH 7.4, 1% deoxycholate, 1% Triton X-100, 0.1% SDS, 5 mM EDTA, 0.15 M NaCl). The lysate was centrifuged to remove insoluble material, and 75 μl of MPL-Sepharose was added as above.

The MPL-Sepharose was then pelleted by low speed centrifugation, and the spent media and cell lysate supernatants were removed. The pellet was washed four times with PBS containing 0.5 M NaCl. After the final wash, the PBS was removed, and 40 μl of 2× sample buffer (10% glycerol, 4% SDS, 50 mM Tris, pH 7.0, 1 mM EDTA, 0.05% bromophenol blue) containing 4% beta-mercaptoethanol was added.

The samples were boiled for five minutes, and 18 μl of each was loaded onto a 10–20% gradient mini-gel (Integrated Separation Systems), then electorphoresed at 100 V for approximately two hours. The gel was fixed for thirty minutes (in 40% methanol, 16% glacial acetic acid in distilled water), then soaked in Amplify™ (Amersham) for twenty minutes. After drying, the gel was exposed to film overnight. A ~70 kD band was highly visible in the lane corresponding to spent media from cells transfected with TPO cDNA. This band was not present from either cell line.

EXAMPLE X

Hematopoeitic Activity of TPO in Normal Mice

BALB/c mice (Simonsen Laboratories, Inc., Gilroy, Calif.) were treated with seven daily intraperitoneal injections of 0.5 ml of either a vehicle control or recombinant TPO. The TPO dose was 12.5 kU of mouse recombinant TPO prepared in 20 mM Tris (pH 8.1), 0.9% NaCl and 0.25% rabbit serum albumin (RSA). Each animal was given a 0.2 ml intraperitoneal injection, once daily with either 12.5 kU TPO or vehicle. On day=0, the animals were bled, and complete blood counts (CBC) were made. On day=6, the animals were bled and sacrificed. CBCs were done and bone marrow and spleen were harvested to analyze progenitor cell colony formation. Results, shown in Table 1, demonstrate that TPO has hematopoietic activity and expands granulocyte/macrophage progenitor cell numbers.

TABLE 1

| | CFU-MK ($\times 10^{-3}$) | | BFU-E ($\times 10^{-3}$) | | CFU-E ($\times 10^{-5}$) | | CFU-GM ($\times 10^{-3}$) | |
| --- | --- | --- | --- | --- | --- | --- | --- | --- |
| | F | S | F | S | F | S | F | S |
| control | 3.4 ± 1.4 | 2.4 ± 0.6 | 2.4 ± 0.8 | 8.2 ± 5.5 | 1.2 ± 0.3 | 1.8 ± 0.7 | 12 ± 1.7 | 1.9 ± 0.5 |
| TPO | 10 ± 1.6* | 32 ± 10* | 4.2 ± 1.1* | 16 ± 4.0 | 0.9 ± 0.2 | 3.7 ± 1.2 | 29 ± 3.1* | 51 ± 27 |

Femoral marrow (F) and splenic (S) progenitor cell numbers values represent the mean number of progenitors±SEM from control vehicle-treated and TPO-treated mice in four experiments of three to five animals each.

EXAMPLE XI

Hematopoietic Activity of TPO in Myelosuppressed Mice

Eight- to twelve-week old, female C57BL/6J or BALB/c mice (Jackson Labs, Bar Harbor, Me.) were irradiated with by exposure to $^{137}$Cs using a Gammacell 40 irradiator (Nordion International Inc., Kanata, Ontario, Canada) and treated with 1.2 mg of carboplatin (Bristol Laboratories, Princeton, N.J.) injected intraperitoneally on day=0. The mice were treated with either recombinant mouse TPO or TPO buffer only and given 0.2 ml intraperitoneal injections. TPO was prepared in a buffer containing 20 mM Tris (pH 8.1), 0.9% NaCl and 0.25% RSA. TPO or TPO buffer was administered on day=1 through day=14. The mice were divided into two groups as follows:

Group 1: Treated with 350 cGy radiation+1.2 mg carboplatin+TPO buffer for 14 days Group 2: Treated with 350 cGy radiation+1.2 mg carboplatin+25 kU TPO/day for 14 days The mice were bled and CBCs were measured on days 0 (to establish baseline), 4, 6, 8, 10, 11 and 13 and then sacrificed. On days 11 and 13 differential cell counts and reticulocyte counts were done. Bone marrow and spleen were harvested for progenitor cell culture.

Results, shown in Table 2, demonstrate that TPO has hematopoietic activity and accelerates the recovery of granulocyte/macrophage progenitor cell numbers.

TABLE 2

|  | CFU-MK ($\times 10^{-3}$) | | BFU-E ($\times 10^{-3}$) | | CFU-E ($\times 10^{-5}$) | | CFU-GM ($\times 10^{-3}$) | |
| --- | --- | --- | --- | --- | --- | --- | --- | --- |
|  | F | S | F | S | F | S | F | S |
| control | 0.11 ± 0.06 | 0.13 ± 0.12 | 0.1 ± 0.08 | 0.20 ± 0.15 | 0.05. ± 0.03 | 0.04 ± 0.03 | 0.7 ± 0.4 | 0.4 ± 0.31 |
| TPO | 1.5 ± 0.5* | 3.1 ± 1.7* | 0.5 ± 0.1* | 2.4 ± 1.3* | 0.5 ± 0.08* | 5.5 ± 2.9* | 5.1 ± 1.1* | 10 ± 4.3* |

The results for femoral (F) and splenic (S) progenitors represent the mean±SEM of three experiments of three to five animals in each group.

EXAMPLE XII

TPO Stimulates Neutrophils in Myelosuppressed Animals

Twenty-five female BALB/c mice (Jackson Labs) were were irradiated by exposure to $^{137}$Cs using a Gammacell 40 irradiator (Nordion International Inc.) and treated with 1.2 mg of carboplatin (Bristol Laboratories) injected intraperitoneally on day=0. The mice were treated with either recombinant human TPO purified as shown in Example II or TPO buffer only (29 mM potassium phosphate, pH 6, containing 0.05% polysorbate 80 and 0.13 M NaCl, and stored frozen) and given one 0.1 ml subcutaneous injection daily. TPO or TPO buffer was administered on day=1 through day=7. The mice were divided into five groups as follows:

Group 1: Treated with 350 cGy radiation+1.2 mg carboplatin+TPO buffer for 7 days (n=5).

Group 2: Treated with 350 cGy radiation+1.2 mg carboplatin+1 kU TPO/kg/day (9 μg TPO/kg) for 7 days (n=5).

Group 3: Treated with 350 cGy radiation+1.2 mg carboplation+5 kU TPO/kg/day (45 μg TPO/kg) for 7 days (n=5).

Group 4: Treated with 350 cGy radiation+1.2 mg carboplatin+10 kU TPO/kg/day (90 μg TPO/kg)for 7 days (n=5).

Group 5: Treated with 350 cGy radiation+1.2 mg carboplatin+20 kU TPO/kg/day (180 μg TPO/kg) for 7 days (n=5).

The mice were prebled on day=0, and baseline CBCs, differential counts and reticulocyte counts were established. The mice were bled for CBCS, differential counts and reticulocyte counts on days 6, 9, 13, 16, and 20.

The results, illustrated in FIGS. 1 and 2, clearly show that TPO-treated animals have increased levels of white blood cells, particularly neutrophils, when compared to animals receiving vehicle. FIG. 1 shows that the total WBC count recovery was increased, in a dose dependent manner with TPO. FIG. 2 shows that at 5–20 kU/kg/day of TPO neutrophil recovery levels were significantly higher than without TPO. Neutrophil recovery started at day=13 in the animals administered 5 kU/kg/day or higher doses of TPO, whereas vehicle treated animals had not begun recovery of neutrophil counts.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of treating neutropenia in a mammal, comprising:
   - determining the number of neutrophils in a mammal to be below $2.0 \times 10^9$/liter, whereby said mammal is identified to be neutropenic;
   - administering to said mammal identified to be neutropenic, an amount of thrombopoietin (TPO) having approximately 330 amino acid residues sufficient to increase the number of neutrophils to at least $2.0 \times 10^9$/liter in said mammal, and
   - monitoring the number of neutrophils in said mammal following said administration.

2. The method of claim 1, wherein the amount of TPO is 0.1–100 µg/kg/day.

3. A method for ex vivo stimulation of neutrophil production comprising culturing bone marrow or peripheral blood cells obtained from a mammal with a composition comprising an amount of thrombopoietin (TPO) having approximately 330 amino acid residues and granulocyte colony-stimulating factor (G-CSF); and
   - measuring the number of neutrophils in said cultured bone marrow or peripheral blood cells, wherein said amount of TPO and G-CSF is sufficient to produce an increase in the number of neutrophils in the bone marrow or peripheral blood cells as compared to bone marrow or peripheral blood cells cultured in the absence of TPO and presence of G-CSF.

4. The method of claim 3, wherein the amount of TPO is 10 pg/ml to 10 ng/ml and the amount of G-CSF is 10–1000 ng/ml.

5. The method of claim 3, wherein the neutrophils are returned to the mammal following chemotherapy.

* * * * *

UNITED STATES PATENT AND TRADEMARK OFFICE
CERTIFICATE OF CORRECTION

PATENT NO. : 5,989,537
DATED : Nov. 23, 1999
INVENTOR(S) : Richard D. Holly, Si Lok, Donald C. Foster, Frederick S. Hagen, Kenneth Kaushansky, Joseph L. Kuijper, Catherine, E. Lofton-Day, Pieter J. Oort, Steven K. Burkhead It is certified that error appears in the above-identified patent and that said Letters Patent is hereby corrected as shown below:

On the title page item [75], delete ", Seattle, all of Wash." and insert therefor --; Steven K. Burkhead, both of Seattle, all of Wash.--

Signed and Sealed this

Ninth Day of January, 2001

Attest:

Q. TODD DICKINSON

*Attesting Officer*  *Commissioner of Patents and Trademarks*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1486 base pairs
      (B) TYPE: nucleic acid
      (C) STRANDEDNESS: double
      (D) TOPOLOGY: linear (ii) MOLECULE TYPE: cDNA (vii) IMMEDIATE SOURCE:
      (B) CLONE: 1081

(ix) FEATURE:
      (A) NAME/KEY: CDS
      (B) LOCATION: 105..1241

(xi) SEQUENCE DESCRIPTION: SEQ ID NO:1:

```
CCTCGTGCCG GTCCTGAGGC CCTTCTCCAC CCGGACAGAG TCCTTGGCCC ACCTCTCTCC        60

CACCCGACTC TGCCGAAAGA AGCACAGAAG CTCAAGCCGC CTCC ATG GCC CCA GGA       116
                                              Met Ala Pro Gly
                                                1
```

```
AAG ATT CAG GGG AGA GGC CCC ATA CAG GGA GCC ACT TCA GTT AGA CAC        164
Lys Ile Gln Gly Arg Gly Pro Ile Gln Gly Ala Thr Ser Val Arg His
 5                  10                  15                  20

CTG GCC AGA ATG GAG CTG ACT GAT TTG CTC CTG GCG GCC ATG CTT CTT        212
Leu Ala Arg Met Glu Leu Thr Asp Leu Leu Leu Ala Ala Met Leu Leu
                    25                  30                  35

GCA GTG GCA AGA CTA ACT CTG TCC AGC CCC GTA GCT CCT GCC TGT GAC        260
Ala Val Ala Arg Leu Thr Leu Ser Ser Pro Val Ala Pro Ala Cys Asp
                40                  45                  50

CCC AGA CTC CTA AAT AAA CTG CTG CGT GAC TCC CAC CTC CTT CAC AGC        308
Pro Arg Leu Leu Asn Lys Leu Leu Arg Asp Ser His Leu Leu His Ser
            55                  60                  65

CGA CTG AGT CAG TGT CCC GAC GTC GAC CCT TTG TCT ATC CCT GTT CTG        356
Arg Leu Ser Gln Cys Pro Asp Val Asp Pro Leu Ser Ile Pro Val Leu
        70                  75                  80

CTG CCT GCT GTG GAC TTT AGC CTG GGA GAA TGG AAA ACC CAG ACG GAA        404
Leu Pro Ala Val Asp Phe Ser Leu Gly Glu Trp Lys Thr Gln Thr Glu
85                  90                  95                 100

CAG AGC AAG GCA CAG GAC ATT CTA GGG GCA GTG TCC CTT CTA CTG GAG        452
Gln Ser Lys Ala Gln Asp Ile Leu Gly Ala Val Ser Leu Leu Leu Glu
                   105                 110                 115

GGA GTG ATG GCA GCA CGA GGA CAG TTG GAA CCC TCC TGC CTC TCA TCC        500
Gly Val Met Ala Ala Arg Gly Gln Leu Glu Pro Ser Cys Leu Ser Ser
                120                 125                 130

CTC CTG GGA CAG CTT TCT GGG CAG GTT CGC CTC CTC TTG GGG GCC CTG        548
Leu Leu Gly Gln Leu Ser Gly Gln Val Arg Leu Leu Leu Gly Ala Leu
            135                 140                 145

CAG GGC CTC CTA GGA ACC CAG CTT CCT CTA CAG GGC AGG ACC ACA GCT        596
Gln Gly Leu Leu Gly Thr Gln Leu Pro Leu Gln Gly Arg Thr Thr Ala
        150                 155                 160

CAC AAG GAC CCC AAT GCC CTC TTC TTG AGC TTG CAA CAA CTG CTT CGG        644
His Lys Asp Pro Asn Ala Leu Phe Leu Ser Leu Gln Gln Leu Leu Arg
165                 170                 175                 180

GGA AAG GTG CGC TTC CTG CTT CTG GTA GAA GGT CCC ACC CTC TGT GTC        692
Gly Lys Val Arg Phe Leu Leu Leu Val Glu Gly Pro Thr Leu Cys Val
                    185                 190                 195

AGA CGG ACC CTG CCA ACC ACA GCT GTC CCA AGC AGT ACT TCT CAA CTC        740
Arg Arg Thr Leu Pro Thr Thr Ala Val Pro Ser Ser Thr Ser Gln Leu
                200                 205                 210

CTC ACA CTA AAC AAG TTC CCA AAC AGG ACT TCT GGA TTG TTG GAG ACG        788
Leu Thr Leu Asn Lys Phe Pro Asn Arg Thr Ser Gly Leu Leu Glu Thr
            215                 220                 225

AAC TTC AGT GTC ACA GCC AGA ACT GCT GGC CCT GGA CTT CTG AGC AGG        836
Asn Phe Ser Val Thr Ala Arg Thr Ala Gly Pro Gly Leu Leu Ser Arg
        230                 235                 240

CTT CAG GGA TTC AGA GTC AAG ATT ACT CCT GGT CAG CTA AAT CAA ACC        884
Leu Gln Gly Phe Arg Val Lys Ile Thr Pro Gly Gln Leu Asn Gln Thr
245                 250                 255                 260

TCC AGG TCC CCA GTC CAA ATC TCT GGA TAC CTG AAC AGG ACA CAC GGA        932
Ser Arg Ser Pro Val Gln Ile Ser Gly Tyr Leu Asn Arg Thr His Gly
                    265                 270                 275

CCT GTG AAT GGA ACT CAT GGG CTC TTT GCT GGA ACC TCA CTT CAG ACC        980
Pro Val Asn Gly Thr His Gly Leu Phe Ala Gly Thr Ser Leu Gln Thr
                280                 285                 290

CTG GAA GCC TCA GAC ATC TCG CCC GGA GCT TTC AAC AAA GGC TCC CTG       1028
Leu Glu Ala Ser Asp Ile Ser Pro Gly Ala Phe Asn Lys Gly Ser Leu
            295                 300                 305

GCA TTC AAC CTC CAG GGT GGA CTT CCT CCT TCT CCA AGC CTT GCT CCT       1076
Ala Phe Asn Leu Gln Gly Gly Leu Pro Pro Ser Pro Ser Leu Ala Pro
        310                 315                 320
```

```
GAT GGA CAC ACA CCC TTC CCT CCT TCA CCT GCC TTG CCC ACC ACC CAT      1124
Asp Gly His Thr Pro Phe Pro Pro Ser Pro Ala Leu Pro Thr Thr His
325                 330                 335                 340

GGA TCT CCA CCC CAG CTC CAC CCC CTG TTT CCT GAC CCT TCC ACC ACC      1172
Gly Ser Pro Pro Gln Leu His Pro Leu Phe Pro Asp Pro Ser Thr Thr
                345                 350                 355

ATG CCT AAC TCT ACC GCC CCT CAT CCA GTC ACA ATG TAC CCT CAT CCC      1220
Met Pro Asn Ser Thr Ala Pro His Pro Val Thr Met Tyr Pro His Pro
            360                 365                 370

AGG AAT TTG TCT CAG GAA ACA TAGCGCGGGC ACTGGCCCAG TGAGCGTCTG         1271
Arg Asn Leu Ser Gln Glu Thr
        375

CAGCTTCTCT CGGGGACAAG CTTCCCCAGG AAGGCTGAGA GGCAGCTGCA TCTGCTCCAG    1331

ATGTTCTGCT TTCACCTAAA AGGCCCTGGG GAAGGGATAC ACAGCACTGG AGATTGTAAA    1391

ATTTTAGGAG CTATTTTTTT TTAACCTATC AGCAATATTC ATCAGAGCAG CTAGCGATCT    1451

TTGGTCTATT TTCGGTATAA ATTTGAAAAT CACTA                              1486

(2) INFORMATION FOR SEQ ID NO:2:

(i) SEQUENCE CHARACTERISTICS:
        (A) LENGTH: 379 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Pro Gly Lys Ile Gln Gly Arg Gly Pro Ile Gln Gly Ala Thr
1               5                   10                  15

Ser Val Arg His Leu Ala Arg Met Glu Leu Thr Asp Leu Leu Leu Ala
            20                  25                  30

Ala Met Leu Leu Ala Val Ala Arg Leu Thr Leu Ser Ser Pro Val Ala
        35                  40                  45

Pro Ala Cys Asp Pro Arg Leu Leu Asn Lys Leu Leu Arg Asp Ser His
    50                  55                  60

Leu Leu His Ser Arg Leu Ser Gln Cys Pro Asp Val Asp Pro Leu Ser
65                  70                  75                  80

Ile Pro Val Leu Leu Pro Ala Val Asp Phe Ser Leu Gly Glu Trp Lys
                85                  90                  95

Thr Gln Thr Glu Gln Ser Lys Ala Gln Asp Ile Leu Gly Ala Val Ser
            100                 105                 110

Leu Leu Leu Glu Gly Val Met Ala Ala Arg Gly Gln Leu Glu Pro Ser
        115                 120                 125

Cys Leu Ser Ser Leu Leu Gly Gln Leu Ser Gly Gln Val Arg Leu Leu
    130                 135                 140

Leu Gly Ala Leu Gln Gly Leu Leu Gly Thr Gln Leu Pro Leu Gln Gly
145                 150                 155                 160

Arg Thr Thr Ala His Lys Asp Pro Asn Ala Leu Phe Leu Ser Leu Gln
                165                 170                 175

Gln Leu Leu Arg Gly Lys Val Arg Phe Leu Leu Leu Val Glu Gly Pro
            180                 185                 190

Thr Leu Cys Val Arg Arg Thr Leu Pro Thr Thr Ala Val Pro Ser Ser
        195                 200                 205

Thr Ser Gln Leu Leu Thr Leu Asn Lys Phe Pro Asn Arg Thr Ser Gly
    210                 215                 220

Leu Leu Glu Thr Asn Phe Ser Val Thr Ala Arg Thr Ala Gly Pro Gly
```

```
                225                 230                 235                 240
Leu Leu Ser Arg Leu Gln Gly Phe Arg Val Lys Ile Thr Pro Gly Gln
                245                 250                 255

Leu Asn Gln Thr Ser Arg Ser Pro Val Gln Ile Ser Gly Tyr Leu Asn
            260                 265                 270

Arg Thr His Gly Pro Val Asn Gly Thr His Gly Leu Phe Ala Gly Thr
            275                 280                 285

Ser Leu Gln Thr Leu Glu Ala Ser Asp Ile Ser Pro Gly Ala Phe Asn
            290                 295                 300

Lys Gly Ser Leu Ala Phe Asn Leu Gln Gly Gly Leu Pro Pro Ser Pro
305                 310                 315                 320

Ser Leu Ala Pro Asp Gly His Thr Pro Phe Pro Pro Ser Pro Ala Leu
            325                 330                 335

Pro Thr Thr His Gly Ser Pro Pro Gln Leu His Pro Leu Phe Pro Asp
            340                 345                 350

Pro Ser Thr Thr Met Pro Asn Ser Thr Ala Pro His Pro Val Thr Met
            355                 360                 365

Tyr Pro His Pro Arg Asn Leu Ser Gln Glu Thr
            370                 375
```

(2) INFORMATION FOR SEQ ID NO:3:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (vii) IMMEDIATE SOURCE:
    (B) CLONE: zc5499

(xi) SEQUENCE DESCRIPTION: SEQ ID NO:3:

CGAGCCACTT TCTGCACTCC TCGAGTTTTT TTTTTTTTTT TT    42

(2) INFORMATION FOR SEQ ID NO:4:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (vii) IMMEDIATE SOURCE:
    (B) CLONE: zc5746

(xi) SEQUENCE DESCRIPTION: SEQ ID NO:4:

GAGAGAGAGA GAGAATTCAT GCCCTCCTGG GCCCTCTTCA TGGTC    45

(2) INFORMATION FOR SEQ ID NO:5:

(i) SEQUENCE CHARACTERISTICS:
    (A) LENGTH: 52 base pairs
    (B) TYPE: nucleic acid
    (C) STRANDEDNESS: single
    (D) TOPOLOGY: linear (vii) IMMEDIATE SOURCE:
    (B) CLONE: zc5762

(xi) SEQUENCE DESCRIPTION: SEQ ID NO:5:

AGAGAGAGAG AGAGCTCGAG TCAAGGCTGC TGCCAATAGC TTAGTGGTAG GT    52

(2) INFORMATION FOR SEQ ID NO:6:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (vii) IMMEDIATE SOURCE:
        (B) CLONE: zc5742

(xi) SEQUENCE DESCRIPTION: SEQ ID NO:6:

GACCCTGGAG CTGCGCCCGC GATCTCGCTA                                     30

(2) INFORMATION FOR SEQ ID NO:7:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (vii) IMMEDIATE SOURCE:
        (B) CLONE: zc6091

(xi) SEQUENCE DESCRIPTION: SEQ ID NO:7:

GAGCACAGAA TTCACTACTC GAGGCGGCCG CTTTTTTTTT TTTTTTTTT                49

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (vii) IMMEDIATE SOURCE:
        (B) CLONE: zc6603

(xi) SEQUENCE DESCRIPTION: SEQ ID NO:8:

GAGGAATTCG CAGAAGCCAT GCCCTCTTGG GCCCTCTTCA TGGTC                    45

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:9:

Val Arg Thr Ser Pro Ala Gly Glu
1               5

(2) INFORMATION FOR SEQ ID NO:10:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (vii) IMMEDIATE SOURCE:
        (B) CLONE: zc6704

(xi) SEQUENCE DESCRIPTION: SEQ ID NO:10:

GAAGAGGAAT TCACCATGGA TGTCTTCTTG CTGGCCTTGG GCACAGAG                 48

(2) INFORMATION FOR SEQ ID NO:11:

(i) SEQUENCE CHARACTERISTICS:
        (A) LENGTH: 60 base pairs
        (B) TYPE: nucleic acid
```

```
            (C) STRANDEDNESS: single
            (D) TOPOLOGY: linear (vii) IMMEDIATE SOURCE:
            (B) CLONE: zc6703

(xi) SEQUENCE DESCRIPTION: SEQ ID NO:11:

CGACTTTACC TCGAGTGCTA CTGATGCTCT TCTGCCAGCA GTCTCGGAGC CCGTGGACAC        60

(2) INFORMATION FOR SEQ ID NO:12:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (vii) IMMEDIATE SOURCE:
            (B) CLONE: zc6707

(xi) SEQUENCE DESCRIPTION: SEQ ID NO:12:

AATTCGCCAT GGGACTCGAG CATCACCATC ACCATCACTG AG                          42

(2) INFORMATION FOR SEQ ID NO:13:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (vii) IMMEDIATE SOURCE:
            (B) CLONE: zc6706

(xi) SEQUENCE DESCRIPTION: SEQ ID NO:13:

GATCCTCAGT GATGGTGATG GTGATGCTCG AGTCCCATGG CG                          42

(2) INFORMATION FOR SEQ ID NO:14:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (vii) IMMEDIATE SOURCE:
            (B) CLONE: zc6172

(xi) SEQUENCE DESCRIPTION: SEQ ID NO:14:

GTCGGTGCTC AGCATTCACT ACTCGAGGGT TTTTTTTTTT TTTTTTT                     47

(2) INFORMATION FOR SEQ ID NO:15:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (vii) IMMEDIATE SOURCE:
            (B) CLONE: zc6936

(xi) SEQUENCE DESCRIPTION: SEQ ID NO:15:

AATTGGCGGC CGCGTCGACT CGTGGATG                                          28

(2) INFORMATION FOR SEQ ID NO:16:

(i) SEQUENCE CHARACTERISTICS:
            (A) LENGTH: 28 base pairs
            (B) TYPE: nucleic acid
```

5,989,537

47

48

-continued (C) STRANDEDNESS: single
        (D) TOPOLOGY: linear (vii) IMMEDIATE SOURCE:
        (B) CLONE: zc6937

(xi) SEQUENCE DESCRIPTION: SEQ ID NO:16:

AATTCATCCA CGAGTCGACG CGGCCGCC                                                28

(2) INFORMATION FOR SEQ ID NO:17:

(i) SEQUENCE CHARACTERISTICS:
        (A) LENGTH: 633 amino acids
        (B) TYPE: amino acid
        (D) TOPOLOGY: linear (ii) MOLECULE TYPE: protein (xi) SEQUENCE DESCRIPTION: SEQ ID NO:17:

Met Pro Ser Trp Ala Leu Phe Met Val Thr Ser Cys Leu Leu Leu Ala
1               5                   10                  15

Leu Pro Asn Gln Ala Gln Val Thr Ser Gln Asp Val Phe Leu Leu Ala
                20                  25                  30

Leu Gly Thr Glu Pro Leu Asn Cys Phe Ser Gln Thr Phe Glu Asp Leu
            35                  40                  45

Thr Cys Phe Trp Asp Glu Glu Ala Ala Pro Ser Gly Thr Tyr Gln
    50                  55                  60

Leu Leu Tyr Ala Tyr Arg Gly Glu Lys Pro Arg Ala Cys Pro Leu Tyr
65                  70                  75                  80

Ser Gln Ser Val Pro Thr Phe Gly Thr Arg Tyr Val Cys Gln Phe Pro
                85                  90                  95

Ala Gln Asp Glu Val Arg Leu Phe Phe Pro Leu His Leu Trp Val Lys
                100                 105                 110

Asn Val Ser Leu Asn Gln Thr Leu Ile Gln Arg Val Leu Phe Val Asp
            115                 120                 125

Ser Val Gly Leu Pro Ala Pro Pro Arg Val Ile Lys Ala Arg Gly Gly
        130                 135                 140

Ser Gln Pro Gly Glu Leu Gln Ile His Trp Glu Ala Pro Ala Pro Glu
145                 150                 155                 160

Ile Ser Asp Phe Leu Arg His Glu Leu Arg Tyr Gly Pro Thr Asp Ser
                165                 170                 175

Ser Asn Ala Thr Ala Pro Ser Val Ile Gln Leu Leu Ser Thr Glu Thr
            180                 185                 190

Cys Cys Pro Thr Leu Trp Met Pro Asn Pro Val Pro Val Leu Asp Gln
        195                 200                 205

Pro Pro Cys Val His Pro Thr Ala Ser Gln Pro His Gly Pro Val Arg
    210                 215                 220

Thr Ser Pro Ala Gly Glu Ala Pro Phe Leu Thr Val Lys Gly Gly Ser
225                 230                 235                 240

Cys Leu Val Ser Gly Leu Gln Ala Gly Lys Ser Tyr Trp Leu Gln Leu
                245                 250                 255

Arg Ser Gln Pro Asp Gly Val Ser Leu Arg Gly Ser Trp Gly Pro Trp
            260                 265                 270

Ser Phe Pro Val Thr Val Asp Leu Pro Gly Asp Ala Val Thr Ile Gly
        275                 280                 285

Leu Gln Cys Phe Thr Leu Asp Leu Lys Met Val Thr Cys Gln Trp Gln
    290                 295                 300

Gln Gln Asp Arg Thr Ser Ser Gln Gly Phe Phe Arg His Ser Arg Thr

```
305                 310                 315                 320
Arg Cys Cys Pro Thr Asp Arg Asp Pro Thr Trp Glu Lys Cys Glu Glu
                325                 330                 335

Glu Glu Pro Arg Pro Gly Ser Gln Pro Ala Leu Val Ser Arg Cys His
            340                 345                 350

Phe Lys Ser Arg Asn Asp Ser Val Ile His Ile Leu Val Glu Val Thr
            355                 360                 365

Thr Ala Gln Gly Ala Val His Ser Tyr Leu Gly Ser Pro Phe Trp Ile
370                 375                 380

His Gln Ala Val Leu Leu Pro Thr Pro Ser Leu His Trp Arg Glu Val
385                 390                 395                 400

Ser Ser Gly Arg Leu Glu Leu Glu Trp Gln His Gln Ser Ser Trp Ala
            405                 410                 415

Ala Gln Glu Thr Cys Tyr Gln Leu Arg Tyr Thr Gly Glu Gly Arg Glu
            420                 425                 430

Asp Trp Lys Val Leu Glu Pro Ser Leu Gly Ala Arg Gly Gly Thr Leu
            435                 440                 445

Glu Leu Arg Pro Arg Ala Arg Tyr Ser Leu Gln Leu Arg Ala Arg Leu
450                 455                 460

Asn Gly Pro Thr Tyr Gln Gly Pro Trp Ser Ala Trp Ser Pro Pro Ala
465                 470                 475                 480

Arg Val Ser Thr Gly Ser Glu Thr Ala Trp Ile Thr Leu Val Thr Ala
            485                 490                 495

Leu Leu Leu Val Leu Ser Leu Ser Ala Leu Leu Gly Leu Leu Leu Leu
            500                 505                 510

Lys Trp Gln Phe Pro Ala His Tyr Arg Arg Leu Arg His Ala Leu Trp
            515                 520                 525

Pro Ser Leu Pro Asp Leu His Arg Val Leu Gly Gln Tyr Leu Arg Asp
530                 535                 540

Thr Ala Ala Leu Ser Pro Ser Lys Ala Thr Val Thr Asp Ser Cys Glu
545                 550                 555                 560

Glu Val Glu Pro Ser Leu Leu Glu Ile Leu Pro Lys Ser Ser Glu Ser
            565                 570                 575

Thr Pro Leu Pro Leu Cys Pro Ser Gln Pro Gln Met Asp Tyr Arg Gly
            580                 585                 590

Leu Gln Pro Cys Leu Arg Thr Met Pro Leu Ser Val Cys Pro Pro Met
            595                 600                 605

Ala Glu Thr Gly Ser Cys Cys Thr Thr His Ile Ala Asn His Ser Tyr
            610                 615                 620

Leu Pro Leu Ser Tyr Trp Gln Gln Pro
625                 630

(2) INFORMATION FOR SEQ ID NO:18:

(i) SEQUENCE CHARACTERISTICS:
        (A) LENGTH: 1062 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1059

(xi) SEQUENCE DESCRIPTION: SEQ ID NO:18:

ATG GAG CTG ACT GAA TTG CTC CTC GTG GTC ATG CTT CTC CTA ACT GCA         48
```

```
        Met Glu Leu Thr Glu Leu Leu Val Val Met Leu Leu Leu Thr Ala
        1               5                  10                 15

AGG CTA ACG CTG TCC AGC CCG GCT CCT CCT GCT TGT GAC CTC CGA GTC         96
Arg Leu Thr Leu Ser Ser Pro Ala Pro Pro Ala Cys Asp Leu Arg Val
                20                  25                  30

CTC AGT AAA CTG CTT CGT GAC TCC CAT GTC CTT CAC AGC AGA CTG AGC        144
Leu Ser Lys Leu Leu Arg Asp Ser His Val Leu His Ser Arg Leu Ser
        35                  40                  45

CAG TGC CCA GAG GTT CAC CCT TTG CCT ACA CCT GTC CTG CTG CCT GCT        192
Gln Cys Pro Glu Val His Pro Leu Pro Thr Pro Val Leu Leu Pro Ala
    50                  55                  60

GTG GAC TTT AGC TTG GGA GAA TGG AAA ACC CAG ATG GAG GAG ACC AAG        240
Val Asp Phe Ser Leu Gly Glu Trp Lys Thr Gln Met Glu Glu Thr Lys
65                  70                  75                  80

GCA CAG GAC ATT CTG GGA GCA GTG ACC CTT CTG CTG GAG GGA GTG ATG        288
Ala Gln Asp Ile Leu Gly Ala Val Thr Leu Leu Leu Glu Gly Val Met
                85                  90                  95

GCA GCA CGG GGA CAA CTG GGA CCC ACT TGC CTC TCA TCC CTC CTG GGG        336
Ala Ala Arg Gly Gln Leu Gly Pro Thr Cys Leu Ser Ser Leu Leu Gly
                100                 105                 110

CAG CTT TCT GGA CAG GTC CGT CTC CTC CTT GGG GCC CTG CAG AGC CTC        384
Gln Leu Ser Gly Gln Val Arg Leu Leu Leu Gly Ala Leu Gln Ser Leu
            115                 120                 125

CTT GGA ACC CAG CTT CCT CCA CAG GGC AGG ACC ACA GCT CAC AAG GAT        432
Leu Gly Thr Gln Leu Pro Pro Gln Gly Arg Thr Thr Ala His Lys Asp
        130                 135                 140

CCC AAT GCC ATC TTC CTG AGC TTC CAA CAC CTG CTC CGA GGA AAG GTG        480
Pro Asn Ala Ile Phe Leu Ser Phe Gln His Leu Leu Arg Gly Lys Val
145                 150                 155                 160

CGT TTC CTG ATG CTT GTA GGA GGG TCC ACC CTC TGC GTC AGG CGG GCC        528
Arg Phe Leu Met Leu Val Gly Gly Ser Thr Leu Cys Val Arg Arg Ala
                165                 170                 175

CCA CCC ACC ACA GCT GTC CCC AGC AGA ACC TCT CTA GTC CTC ACA CTG        576
Pro Pro Thr Thr Ala Val Pro Ser Arg Thr Ser Leu Val Leu Thr Leu
                180                 185                 190

AAC GAG CTC CCA AAC AGG ACT TCT GGA TTG TTG GAG ACA AAC TTC ACT        624
Asn Glu Leu Pro Asn Arg Thr Ser Gly Leu Leu Glu Thr Asn Phe Thr
            195                 200                 205

GCC TCA GCC AGA ACT ACT GGC TCT GGG CTT CTG AAG TGG CAG CAG GGA        672
Ala Ser Ala Arg Thr Thr Gly Ser Gly Leu Leu Lys Trp Gln Gln Gly
210                 215                 220

TTC AGA GCC AAG ATT CCT GGT CTG CTG AAC CAA ACC TCC AGG TCC CTG        720
Phe Arg Ala Lys Ile Pro Gly Leu Leu Asn Gln Thr Ser Arg Ser Leu
225                 230                 235                 240

GAC CAA ATC CCC GGA TAC CTG AAC AGG ATA CAC GAA CTC TTG AAT GGA        768
Asp Gln Ile Pro Gly Tyr Leu Asn Arg Ile His Glu Leu Leu Asn Gly
            245                 250                 255

ACT CGT GGA CTC TTT CCT GGA CCC TCA CGC AGG ACC CTA GGA GCC CCG        816
Thr Arg Gly Leu Phe Pro Gly Pro Ser Arg Arg Thr Leu Gly Ala Pro
            260                 265                 270

GAC ATT TCC TCA GGA ACA TCA GAC ACA GGC TCC CTG CCA CCC AAC CTC        864
Asp Ile Ser Ser Gly Thr Ser Asp Thr Gly Ser Leu Pro Pro Asn Leu
            275                 280                 285

CAG CCT GGA TAT TCT CCT TCC CCA ACC CAT CCT CCT ACT GGA CAG TAT        912
Gln Pro Gly Tyr Ser Pro Ser Pro Thr His Pro Pro Thr Gly Gln Tyr
        290                 295                 300

ACG CTC TTC CCT CTT CCA CCC ACC TTG CCC ACC CCT GTG GTC CAG CTC        960
Thr Leu Phe Pro Leu Pro Pro Thr Leu Pro Thr Pro Val Val Gln Leu
305                 310                 315                 320

CAC CCC CTG CTT CCT GAC CCT TCT GCT CCA ACG CCC ACC CCT ACC AGC       1008
```

```
His Pro Leu Leu Pro Asp Pro Ser Ala Pro Thr Pro Thr Pro Thr Ser
                325                 330                 335

CCT CTT CTA AAC ACA TCC TAC ACC CAC TCC CAG AAT CTG TCT CAG GAA    1056
Pro Leu Leu Asn Thr Ser Tyr Thr His Ser Gln Asn Leu Ser Gln Glu
                340                 345                 350

GGG TAA                                                            1062
Gly
```

(2) INFORMATION FOR SEQ ID NO:19:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:19:

```
Met Glu Leu Thr Glu Leu Leu Val Val Met Leu Leu Leu Thr Ala
 1               5                  10                  15

Arg Leu Thr Leu Ser Ser Pro Ala Pro Pro Ala Cys Asp Leu Arg Val
                20                  25                  30

Leu Ser Lys Leu Leu Arg Asp Ser His Val Leu His Ser Arg Leu Ser
                35                  40                  45

Gln Cys Pro Glu Val His Pro Leu Pro Thr Pro Val Leu Leu Pro Ala
 50                  55                  60

Val Asp Phe Ser Leu Gly Glu Trp Lys Thr Gln Met Glu Glu Thr Lys
 65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
                100                 105                 110

Gln Leu Ser Gly Gln Val Arg Leu Leu Leu Gly Ala Leu Gln Ser Leu
                115                 120                 125

Leu Gly Thr Gln Leu Pro Pro Gln Gly Arg Thr Thr Ala His Lys Asp
                130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
                180                 185                 190

Asn Glu Leu Pro Asn Arg Thr Ser Gly Leu Leu Glu Thr Asn Phe Thr
                195                 200                 205

Ala Ser Ala Arg Thr Thr Gly Ser Gly Leu Leu Lys Trp Gln Gln Gly
                210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
                260                 265                 270

Asp Ile Ser Ser Gly Thr Ser Asp Thr Gly Ser Leu Pro Pro Asn Leu
                275                 280                 285

Gln Pro Gly Tyr Ser Pro Ser Pro Thr His Pro Pro Thr Gly Gln Tyr
                290                 295                 300

Thr Leu Phe Pro Leu Pro Pro Thr Leu Pro Thr Pro Val Val Gln Leu
```

```
305                310               315                 320
His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
            340                 345                 350

Gly (2) INFORMATION FOR SEQ ID NO:20:

(i) SEQUENCE CHARACTERISTICS:
        (A) LENGTH: 4823 base pairs
        (B) TYPE: nucleic acid
        (C) STRANDEDNESS: double
        (D) TOPOLOGY: linear (ii) MOLECULE TYPE: DNA (genomic)

(ix) FEATURE:
         (A) NAME/KEY: CDS
         (B) LOCATION: join(632..644, 876..1003, 1290..1376,
             3309..3476, 3713..4375)

(xi) SEQUENCE DESCRIPTION: SEQ ID NO:20:
```

| | |
|---|---|
| CTTTCTTGCT TTCTTTCTTT CTTTCTTTCT TTCTTTTTTT TTTTTGAGAC GGAGTTTCAC | 60 |
| TCTTATTGCC CAGGCTGGAG TGCAATGGTG CGATCTCGGC TCACCACAAC CTCCGCCTCC | 120 |
| CAGGTACAAG CGATTCTCCT GTCTCAGCCT CCCAAGTAGC TTGGATTACA GGCATGAACC | 180 |
| ACCACACCCT GCTAGTTTTT TTGTATTTCG TAGAGCCGGG GTTTCACCAT GTTAGTGAGG | 240 |
| CTGGTGGCGA ACTCCTGACC TCAGGTGATC CACCCGCCTT GGACTCCAA AGTGCTGGGA | 300 |
| TTACAGGCAT GAGCCACTGC ACCCGGCACA CCATATGCTT TCATCACAAG AAAATGTGAG | 360 |
| AGAATTCAGG GCTTTGGCAG TTCCAGGCTG GTCAGCATCT CAAGCCCTCC CCAGCATCTG | 420 |
| TTCACCCTGC CAGGCAGTCT CTTCCTAGAA ACTTGGTTAA ATGTTCACTC TTCTTGCTAC | 480 |
| TTTCAGGATA GATTCTTCAC CCTTGGTCCG CCTTTGCCCC ACCCTACTCT GCCCAGAAGT | 540 |
| GCAAGAGCCT AAGCCGCCTC CATGGCCCCA GGAAGGATTC AGGGGAGAGG CCCCAAACAG | 600 |
| GGAGCCACGC CAGCCAGACA CCCCGGCCAG A ATG GAG CTG ACT G GTGAGAACAC | 654 |
|                                                            Met Glu Leu Thr<br>                                                             1 | |
| ACCTGAGGGG CTAGGGCCAT ATGGAAACAT GACAGAAGGG GAGAGAGAAA GGAGACACGC | 714 |
| TGCAGGGGGC AGGAAGCTGG GGGAACCCAT TCTCCCAAAA ATAAGGGGTC TGAGGGGTGG | 774 |
| ATTCCCTGGG TTTCAGGTCT GGGTCCTGAA TGGGAATTCC TGGAATACCA GCTGACAATG | 834 |
| ATTTCCTCCT CATCTTTCAA CCTCACCTCT CCTCATCTAA G AA TTG CTC CTC | 886 |
|                                                          Glu Leu Leu Leu<br>                                                           5 | |
| GTG GTC ATG CTT CTC CTA ACT GCA AGG CTA ACG CTG TCC AGC CCG GCT<br>Val Val Met Leu Leu Leu Thr Ala Arg Leu Thr Leu Ser Ser Pro Ala<br>    10               15               20 | 934 |
| CCT CCT GCT TGT GAC CTC CGA GTC CTC AGT AAA CTG CTT CGT GAC TCC<br>Pro Pro Ala Cys Asp Leu Arg Val Leu Ser Lys Leu Leu Arg Asp Ser<br>25              30              35               40 | 982 |
| CAT GTC CTT CAC AGC AGA CTG GTGAGAACTC CCAACATTAT CCCCTTTATC<br>His Val Leu His Ser Arg Leu<br>                45 | 1033 |
| CGCGTAACTG GTAAGACACC CATACTCCCA GGAAGACACC ATCACTTCCT CTAACTCCTT | 1093 |
| GACCCAATGA CTATTCTTCC CATATTGTCC CCACCTACTG ATCACACTCT CTGACAAGGA | 1153 |
| TTATTCTTCA CAATACAGCC CGCATTTAAA AGCTCTCGTC TAGAGATAGT ACTCATGGAG | 1213 |

-continued

```
GACTAGCCTG CTTATTAGGC TACCATAGCT CTCTCTATTT CAGCTCCCTT CTCCCCCCAC    1273

CAATCTTTTT CAACAG AGC CAG TGC CCA GAG GTT CAC CCT TTG CCT ACA        1322
              Ser Gln Cys Pro Glu Val His Pro Leu Pro Thr
                  50                      55

CCT GTC CTG CTG CCT GCT GTG GAC TTT AGC TTG GGA GAA TGG AAA ACC     1370
Pro Val Leu Leu Pro Ala Val Asp Phe Ser Leu Gly Glu Trp Lys Thr
    60              65                  70

CAG ATG GTAAGAAAGC CATCCCTAAC CTTGGCTTCC CTAAGTCCTG TCTTCAGTTT      1426
Gln Met
75

CCCACTGCTT CCCATGGATT CTCCAACATT CTTGAGCTTT TTAAAAATAT CTCACCTTCA    1486

GCTTGGCCAC CCTAACCCAA TCTACATTCA CCTATGATGA TAGCCTGTGG ATAAGATGAT    1546

GGCTTGCAGG TCCAATATGT GAATAGATTT GAAGCTGAAC ACCATGAAAA GCTGGAGAGA    1606

AATCGCTCAT GGCCATGCCT TTGACCTATT CCCGTTCAGT CTTCTTAAAT TGGCATGAAG    1666

AAGCAAGACT CATATGTCAT CCACAGATGA CACAAAGCTG GGAAGTACCA CTAAAATAAC    1726

AAAAGACTGA ATCAAGATTC AAATCACTGA AGACTAGGT CAAAAACAAG GTGAAACAAC     1786

AGAGATATAA ACTTCTACAT GTGGGCCGGG GGCTCACGCC TGTAATCCCA GCACTTTGGG    1846

AGGCCGAGGC AGGCAGATCA CCTGAGGGCA GGAGTTTGAG AGCAGCCTGG CCAACATGGC    1906

GAAACCCCGT CTCTACTAAG AATACAGAAT TAGCCGGGCA TGGTAGTGCA TGCCTGTAAT    1966

CCCAGCTACT TGGAAGGCTG AAGCAGGAGA ATCCCTTGAA CCCAGGAGGT GGAGGTTGTA    2026

GTGAGCTGAG ATCATGCCAA TGCACTCCAG CCTGGGTGAC AAGAGCAAAA CTCCGTCTCA    2086

AAAAGAAAAA AAAATTCTAC ATGTGTAAAT TAATGAGTAA AGTCCTATTC CAGCTTTCAG    2146

GCCACAATGC CCTGCTTCCA TCATTTAAGC CTCTGGCCCT AGCACTTCCT ACGAAAAGGA    2206

TCTGAGAGAA TTAAATTGCC CCCAAACTTA CCATGTAACA TTACTGAAGC TGCTATTCTT    2266

AAAGCTAGTA ATTCTTGTCT GTTTGATGTT TAGCATCCCC ATTGTGGAAA TGCTCGTACA    2326

GAACTCTATT CCGAGTGGAC TACACTTAAA TATACTGGCC TGAACACCGG ACATCCCCCT    2386

GAAGACATAT GCTAATTTAT TAAGAGGGAC CATATTAAAC TAACATGTGT CTAGAAAGCA    2446

GCAGCCTGAA CAGAAAGAGA CTAGAAGCAT GTTTTATGGG CAATAGTTTA AAAAACTAAA    2506

ATCTATCCTC AAGAACCCTA GCGTCCCTTC TTCCTTCAGG ACTGAGTCAG GGAAGAAGGG    2566

CAGTTCCTAT GGGTCCCTTC TAGTCCTTTC TTTTCATCCT TATGATCATT ATGGTAGAGT    2626

CTCATACCTA CATTTAGTTT ATTTATTATT ATTATTTGAG ACGGAGTCTC ACTCTATCCC    2686

CCAGGCTGGA GTGCAGTGGC ATGATCTCAA CTCACTGCAA CCTCAGCCTC CCGGATTCAA    2746

GCGATTCTCC TGTCTCAGTC TCCCAAGTAG CTGGGATTAC AGGTGCCCAC CACCATGCCC    2806

AGCTAATTTG TGTATTTGTG GTAGAGATGG GGTTTCACCA TGTTGGGCAG GCTGATCTTG    2866

AACTCCTGAC CTCAGGTGAT CCACCTGCCT CAGCCTCCCA AAGTGCTGGG ATTACAGGCG    2926

TGAGCCACTG CACCCAGCCT TCATTCAGTT TAAAAATCAA ATGATCCTAA GGTTTTGCAG    2986

CAGAAAGAGT AAATTTGCAG CACTAGAACC AAGAGGTAAA AGCTGTAACA GGGCAGATTT    3046

CAGCAACGTA AGAAAAAAGG AGCTCTTCTC ACTGAAACCA AGTGTAAGAC CAGGCTGGAC    3106

TAGAGGACAC GGGAGTTTTT GAAGCAGAGG CTGATGACCA GCTGTCGGGA GACTGTGAAG    3166

GAATTCCTGC CCTGGGTGGG ACCTTGGTCC TGTCCAGTTC TCAGCCTGTA TGATTCACTC    3226

TGCTGGCTAC TCCTAAGGCT CCCCACCCGC TTTTAGTGTG CCCTTTGAGG CAGTGCGCTT    3286

CTCTCTTCCA TCTCTTTCTC AG GAG GAG ACC AAG GCA CAG GAC ATT CTG GGA   3338
                          Glu Glu Thr Lys Ala Gln Asp Ile Leu Gly
                           80                  85
```

```
GCA GTG ACC CTT CTG CTG GAG GGA GTG ATG GCA GCA CGG GGA CAA CTG         3386
Ala Val Thr Leu Leu Leu Glu Gly Val Met Ala Ala Arg Gly Gln Leu
             90                  95                 100

GGA CCC ACT TGC CTC TCA TCC CTC CTG GGG CAG CTT TCT GGA CAG GTC         3434
Gly Pro Thr Cys Leu Ser Ser Leu Leu Gly Gln Leu Ser Gly Gln Val
        105                 110                 115

CGT CTC CTC CTT GGG GCC CTG CAG AGC CTC CTT GGA ACC CAG                 3476
Arg Leu Leu Leu Gly Ala Leu Gln Ser Leu Leu Gly Thr Gln
    120                 125                 130

GTAAGTCCCC AGTCAAGGGA TCTGTAGAAA CTGTTCTTTT CTGACTCAGT CCCCCTAGAA       3536

GACCTGAGGG AAGAAGGGCT CTTCCAGGGA GCTCAAGGGC AGAAGAGCTG ATCTACTAAG       3596

AGTGCTCCCT GCCAGCCACA ATGCCTGGGT ACTGGCATCC TGTCTTTCCT ACTTAGACAA       3656

GGGAGGCCTG AGATCTGGCC CTGGTGTTTG GCCTCAGGAC CATCCTCTGC CCTCAG           3712

CTT CCT CCA CAG GGC AGG ACC ACA GCT CAC AAG GAT CCC AAT GCC ATC         3760
Leu Pro Pro Gln Gly Arg Thr Thr Ala His Lys Asp Pro Asn Ala Ile
            135                 140                 145

TTC CTG AGC TTC CAA CAC CTG CTC CGA GGA AAG GTG CGT TTC CTG ATG         3808
Phe Leu Ser Phe Gln His Leu Leu Arg Gly Lys Val Arg Phe Leu Met
        150                 155                 160

CTT GTA GGA GGG TCC ACC CTC TGC GTC AGG CGG GCC CCA CCC ACC ACA         3856
Leu Val Gly Gly Ser Thr Leu Cys Val Arg Arg Ala Pro Pro Thr Thr
165                 170                 175                 180

GCT GTC CCC AGC AGA ACC TCT CTA GTC CTC ACA CTG AAC GAG CTC CCA         3904
Ala Val Pro Ser Arg Thr Ser Leu Val Leu Thr Leu Asn Glu Leu Pro
                185                 190                 195

AAC AGG ACT TCT GGA TTG TTG GAG ACA AAC TTC ACT GCC TCA GCC AGA         3952
Asn Arg Thr Ser Gly Leu Leu Glu Thr Asn Phe Thr Ala Ser Ala Arg
            200                 205                 210

ACT ACT GGC TCT GGG CTT CTG AAG TGG CAG CAG GGA TTC AGA GCC AAG         4000
Thr Thr Gly Ser Gly Leu Leu Lys Trp Gln Gln Gly Phe Arg Ala Lys
        215                 220                 225

ATT CCT GGT CTG CTG AAC CAA ACC TCC AGG TCC CTG GAC CAA ATC CCC         4048
Ile Pro Gly Leu Leu Asn Gln Thr Ser Arg Ser Leu Asp Gln Ile Pro
    230                 235                 240

GGA TAC CTG AAC AGG ATA CAC GAA CTC TTG AAT GGA ACT CGT GGA CTC         4096
Gly Tyr Leu Asn Arg Ile His Glu Leu Leu Asn Gly Thr Arg Gly Leu
245                 250                 255                 260

TTT CCT GGA CCC TCA CGC AGG ACC CTA GGA GCC CCG GAC ATT TCC TCA         4144
Phe Pro Gly Pro Ser Arg Arg Thr Leu Gly Ala Pro Asp Ile Ser Ser
                265                 270                 275

GGA ACA TCA GAC ACA GGC TCC CTG CCA CCC AAC CTC CAG CCT GGA TAT         4192
Gly Thr Ser Asp Thr Gly Ser Leu Pro Pro Asn Leu Gln Pro Gly Tyr
            280                 285                 290

TCT CCT TCC CCA ACC CAT CCT CCT ACT GGA CAG TAT ACG CTC TTC CCT         4240
Ser Pro Ser Pro Thr His Pro Pro Thr Gly Gln Tyr Thr Leu Phe Pro
        295                 300                 305

CTT CCA CCC ACC TTG CCC ACC CCT GTG GTC CAG CTC CAC CCC CTG CTT         4288
Leu Pro Pro Thr Leu Pro Thr Pro Val Val Gln Leu His Pro Leu Leu
    310                 315                 320

CCT GAC CCT TCT GCT CCA ACG CCC ACC CCT ACC AGC CCT CTT CTA AAC         4336
Pro Asp Pro Ser Ala Pro Thr Pro Thr Pro Thr Ser Pro Leu Leu Asn
325                 330                 335                 340

ACA TCC TAC ACC CAC TCC CAG AAT CTG TCT CAG GAA GGG TAAGGTTCTC          4385
Thr Ser Tyr Thr His Ser Gln Asn Leu Ser Gln Glu Gly
                345                 350

AGACACTGCC GACATCAGCA TTGTCTCGTG TACAGCTCCC TTCCCTGCAG GGCGCCCCTG       4445

GGAGACAACT GGACAAGATT TCCTACTTTC TCCTGAAACC CAAAGCCCTG GTAAAAGGGA       4505
```

```
TACACAGGAC TGAAAAGGGA ATCATTTTTC ACTGTACATT ATAAACCTTC AGAAGCTATT      4565

TTTTTAAGCT ATCAGCAATA CTCATCAGAG CAGCTAGCTC TTTGGTCTAT TTTCTGCAGA      4625

AATTTGCAAC TCACTGATTC TCAACATGCT CTTTTTCTGT GATAACTCTG CAAAGACCTG      4685

GGCTGGCCTG GCAGTTGAAC AGAGGGAGAG ACTAACCTTG AGTCAGAAAA CAGAGGAAGG      4745

GTAATTTCCT TGCTTCAAA TTCAAGGCCT TCCAACGCCC CCATCCCCTT TACTATCATT       4805

CTCAGTGGGA CTCTGATC                                                    4823
```

(2) INFORMATION FOR SEQ ID NO:21:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:21:

```
Met Glu Leu Thr Glu Leu Leu Val Val Met Leu Leu Thr Ala
1               5                   10                  15

Arg Leu Thr Leu Ser Ser Pro Ala Pro Ala Cys Asp Leu Arg Val
                20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65              70                  75                  80

Ala Gln Asp Ile Leu Gly Ala Val Thr Leu Leu Glu Gly Val Met
                85                  90                  95

Ala Ala Arg Gly Gln Leu Gly Pro Thr Cys Leu Ser Ser Leu Leu Gly
                100                 105                 110

Gln Leu Ser Gly Gln Val Arg Leu Leu Leu Gly Ala Leu Gln Ser Leu
            115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
                180                 185                 190

Asn Glu Leu Pro Asn Arg Thr Ser Gly Leu Leu Glu Thr Asn Phe Thr
            195                 200                 205

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
                260                 265                 270

Asp Ile Ser Ser Gly Thr Ser Asp Thr Gly Ser Leu Pro Pro Asn Leu
            275                 280                 285

Gln Pro Gly Tyr Ser Pro Ser Pro Thr His Pro Pro Thr Gly Gln Tyr
    290                 295                 300
```

```
Thr Leu Phe Pro Leu Pro Pro Thr Leu Pro Thr Pro Val Val Gln Leu
305                 310                315                 320

His Pro Leu Leu Pro Asp Pro Ser Ala Pro Thr Pro Thr Pro Thr Ser
            325                 330                 335

Pro Leu Leu Asn Thr Ser Tyr Thr His Ser Gln Asn Leu Ser Gln Glu
                340                 345                 350

Gly
```